US011786695B2

United States Patent
Bulman et al.

(10) Patent No.: US 11,786,695 B2
(45) Date of Patent: Oct. 17, 2023

(54) METHODS OF MAKING AN EXPANDABLE SHEATH

(71) Applicant: Edwards Lifesciences Corporation, Irvine, CA (US)

(72) Inventors: Erik Bulman, Lake Forest, CA (US); Duy Nguyen, Corona, CA (US); Kim D. Nguyen, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 592 days.

(21) Appl. No.: 16/514,021

(22) Filed: Jul. 17, 2019

(65) Prior Publication Data

US 2020/0030572 A1 Jan. 30, 2020

Related U.S. Application Data

(60) Provisional application No. 62/702,993, filed on Jul. 25, 2018.

(51) Int. Cl.
*A61M 25/00* (2006.01)
*B29C 48/00* (2019.01)
(Continued)

(52) U.S. Cl.
CPC ....... *A61M 25/0009* (2013.01); *A61F 2/2436* (2013.01); *B29C 48/0021* (2019.02);
(Continued)

(58) Field of Classification Search
CPC ........ B29C 48/021; B29C 48/09; B29C 48/21
See application file for complete search history.

(56) References Cited

U.S. PATENT DOCUMENTS 4,601,713 A 7/1986 Fuqua
4,710,181 A 12/1987 Fuqua
(Continued)

FOREIGN PATENT DOCUMENTS

EP 0103546 A1 3/1984
EP 0177177 A2 4/1986
(Continued)

OTHER PUBLICATIONS

510K Premarket Notification, Jun. 22, 2018.
BSX Structural Heart Update 2018.

*Primary Examiner* — Barbara J Musser
(74) *Attorney, Agent, or Firm* — Meunier Carlin Curfman LLC; Sean Seung Kyu Kim

(57) ABSTRACT

Disclosed herein are expandable introducer sheaths and methods of making and using the same. The sheaths minimize trauma to a patient's vasculature by allowing for temporary expansion of a portion of the sheath to accommodate passage of a delivery system for a cardiovascular device, then return to a non-expanded state after the passage of the device. The sheath includes an elongated annular member through which the cardiovascular device and its delivery system pass. In an embodiment, the annular inner member can be formed by coextruding a first and second material. The first material includes a fold, and the second material radially spaces the different parts of the fold from each other during fabrication and provides support for maintaining the tubular structure. The second material is removed once the coextrusion process is complete.

19 Claims, 12 Drawing Sheets

(51) Int. Cl.
  *B29C 48/21* (2019.01)
  *A61F 2/24* (2006.01)
  *B29C 48/09* (2019.01)
  *B29L 31/00* (2006.01)

(52) U.S. Cl.
  CPC .............. *B29C 48/09* (2019.02); *B29C 48/21* (2019.02); *B29L 2031/7542* (2013.01)

(56) References Cited

U.S. PATENT DOCUMENTS

| | | | |
|---|---|---|---|
| 4,716,901 | A | 1/1988 | Jackson et al. |
| 4,738,666 | A | 4/1988 | Fuqua |
| 4,921,479 | A | 5/1990 | Grayzel |
| 5,104,388 | A | 4/1992 | Quackenbush |
| 5,158,545 | A | 10/1992 | Trudell et al. |
| 5,176,659 | A | 1/1993 | Mancini |
| 5,217,468 | A | 6/1993 | Clement |
| 5,234,425 | A | 8/1993 | Fogarty et al. |
| 5,256,150 | A | 10/1993 | Quiachon et al. |
| 5,318,588 | A * | 6/1994 | Horzewski ........ A61M 25/0662 606/198 |
| 5,320,611 | A | 6/1994 | Bonutti et al. |
| 5,380,304 | A | 1/1995 | Parker |
| 5,501,667 | A | 3/1996 | Verduin, Jr. |
| 5,514,091 | A | 5/1996 | Yoon |
| 5,514,236 | A | 5/1996 | Avellanet et al. |
| 5,674,240 | A | 10/1997 | Bonutti et al. |
| 5,810,776 | A | 9/1998 | Bacich et al. |
| 5,817,100 | A | 10/1998 | Igaki |
| 5,827,227 | A | 10/1998 | DeLago |
| 5,895,410 | A | 4/1999 | Forber et al. |
| 5,964,730 | A | 10/1999 | Williams et al. |
| 5,997,508 | A | 12/1999 | Lunn et al. |
| 6,080,141 | A | 6/2000 | Castro et al. |
| 6,090,072 | A | 7/2000 | Kratoska et al. |
| 6,090,136 | A | 7/2000 | McDonald et al. |
| 6,190,357 | B1 | 2/2001 | Ferrari et al. |
| 6,312,443 | B1 | 11/2001 | Stone |
| 6,346,092 | B1 | 2/2002 | Leschinsky |
| 6,358,238 | B1 | 3/2002 | Sherry |
| 6,443,979 | B1 | 9/2002 | Stalker et al. |
| 6,494,860 | B2 | 12/2002 | Rocamora et al. |
| 6,632,236 | B2 | 10/2003 | Hogendijk et al. |
| 6,652,492 | B1 | 11/2003 | Bell et al. |
| 6,814,715 | B2 | 11/2004 | Bonutti et al. |
| 6,899,727 | B2 | 5/2005 | Armstrong et al. |
| 7,144,386 | B2 | 12/2006 | Korkor et al. |
| 7,329,268 | B2 | 2/2008 | Van Nguyen et al. |
| 7,438,712 | B2 | 10/2008 | Chouinard |
| 7,534,250 | B2 | 5/2009 | Schaeffer et al. |
| 7,591,832 | B2 | 9/2009 | Eversull et al. |
| 7,655,016 | B2 | 2/2010 | Demarais et al. |
| 7,678,128 | B2 | 3/2010 | Boyle et al. |
| 7,713,193 | B2 | 5/2010 | Nance et al. |
| 7,762,995 | B2 | 7/2010 | Eversull et al. |
| 7,766,820 | B2 * | 8/2010 | Core ................. A61M 25/0023 600/140 |
| 7,780,692 | B2 | 8/2010 | Nance et al. |
| 7,785,360 | B2 | 8/2010 | Freitag |
| 7,837,692 | B2 | 11/2010 | Mulholland et al. |
| 7,892,203 | B2 | 2/2011 | Lenker et al. |
| 7,927,309 | B2 | 4/2011 | Palm |
| 7,963,952 | B2 | 6/2011 | Wright, Jr. et al. |
| 8,034,072 | B2 | 10/2011 | Nguyen et al. |
| 8,048,034 | B2 | 11/2011 | Eversull et al. |
| 8,090,936 | B2 | 1/2012 | Fallon et al. |
| 8,092,481 | B2 | 1/2012 | Nance et al. |
| 8,252,015 | B2 | 8/2012 | Leeflang et al. |
| 8,282,664 | B2 | 10/2012 | Nance et al. |
| 8,414,645 | B2 | 4/2013 | Dwork et al. |
| 8,562,559 | B2 | 10/2013 | Bishop et al. |
| 8,562,673 | B2 | 10/2013 | Yeung et al. |
| 8,652,203 | B2 | 2/2014 | Quadri et al. |
| 8,668,668 | B2 | 3/2014 | Bishop et al. |
| 8,690,936 | B2 | 4/2014 | Nguyen et al. |
| 8,790,387 | B2 | 7/2014 | Nguyen et al. |
| 9,044,577 | B2 | 6/2015 | Bishop et al. |
| 9,192,751 | B2 | 11/2015 | Macaulay et al. |
| 9,192,752 | B2 | 11/2015 | Leeflang et al. |
| 9,254,374 | B2 | 2/2016 | Thorstenson et al. |
| 9,259,813 | B2 | 2/2016 | Heideman et al. |
| 9,301,840 | B2 | 4/2016 | Nguyen et al. |
| 9,301,841 | B2 | 4/2016 | Nguyen et al. |
| 9,320,508 | B2 | 4/2016 | Carroux |
| 9,393,041 | B2 | 7/2016 | Barker et al. |
| 9,642,704 | B2 | 5/2017 | Tuval et al. |
| 9,788,944 | B2 | 10/2017 | Daly et al. |
| 9,907,931 | B2 | 3/2018 | Birmingham et al. |
| 9,987,134 | B2 | 6/2018 | Nguyen et al. |
| 10,517,720 | B2 | 12/2019 | Nguyen et al. |
| 10,524,905 | B2 | 1/2020 | Nguyen et al. |
| 10,524,906 | B2 | 1/2020 | Nguyen et al. |
| 10,524,907 | B2 | 1/2020 | Nguyen et al. |
| 10,792,150 | B2 | 10/2020 | Nguyen et al. |
| 11,045,317 | B2 | 6/2021 | Nguyen et al. |
| 2001/0004703 | A1 | 6/2001 | Tiernan |
| 2002/0032459 | A1 | 3/2002 | Horzewski et al. |
| 2002/0123793 | A1 | 9/2002 | Schaldach et al. |
| 2003/0004537 | A1 | 1/2003 | Boyle et al. |
| 2004/0087968 | A1 | 5/2004 | Core |
| 2004/0122415 | A1 | 6/2004 | Johnson |
| 2005/0080430 | A1 | 4/2005 | Wright et al. |
| 2005/0085842 | A1 | 4/2005 | Eversull et al. |
| 2005/0124937 | A1 | 6/2005 | Kick et al. |
| 2005/0125021 | A1 | 6/2005 | Nance et al. |
| 2005/0222576 | A1 | 10/2005 | Kick et al. |
| 2006/0020321 | A1 | 1/2006 | Parker |
| 2006/0052750 | A1 | 3/2006 | Lenker et al. |
| 2006/0135962 | A1 | 6/2006 | Kick et al. |
| 2006/0135981 | A1 | 6/2006 | Lenker et al. |
| 2006/0217755 | A1 | 9/2006 | Eversull et al. |
| 2007/0021768 | A1 | 1/2007 | Nance et al. |
| 2007/0074805 | A1 | 4/2007 | Leeflang et al. |
| 2007/0087148 | A1 | 4/2007 | Okushi et al. |
| 2007/0112422 | A1 | 5/2007 | Dehdashtian et al. |
| 2008/0004521 | A1 | 1/2008 | Hundley et al. |
| 2008/0004571 | A1 | 1/2008 | Voss |
| 2008/0114331 | A1 | 5/2008 | Holman et al. |
| 2008/0200943 | A1 | 8/2008 | Barker et al. |
| 2008/0243081 | A1 | 10/2008 | Nance et al. |
| 2008/0255447 | A1 | 10/2008 | Bourang et al. |
| 2008/0300544 | A1 | 12/2008 | Palm |
| 2009/0287182 | A1 | 11/2009 | Bishop et al. |
| 2010/0049313 | A1 | 2/2010 | Alon et al. |
| 2010/0094209 | A1 | 4/2010 | Drasler et al. |
| 2010/0094392 | A1 | 4/2010 | Nguyen et al. |
| 2010/0198160 | A1 | 8/2010 | Voss |
| 2011/0112567 | A1 | 5/2011 | Lenker et al. |
| 2011/0190697 | A1 | 8/2011 | Farnan |
| 2011/0251681 | A1 | 10/2011 | Shipley et al. |
| 2012/0116439 | A1 | 5/2012 | Ho |
| 2012/0158033 | A1 | 6/2012 | Deal et al. |
| 2012/0323180 | A1 | 12/2012 | Chebator et al. |
| 2013/0030369 | A1 | 1/2013 | Root et al. |
| 2013/0131718 | A1 | 5/2013 | Jenson et al. |
| 2013/0178711 | A1 | 7/2013 | Avneri et al. |
| 2013/0231735 | A1 | 9/2013 | Deem et al. |
| 2013/0281787 | A1 | 10/2013 | Avneri et al. |
| 2014/0121629 | A1 | 5/2014 | Macaulay et al. |
| 2014/0236122 | A1 | 8/2014 | Anderson et al. |
| 2014/0236123 | A1 | 8/2014 | Birmingham et al. |
| 2014/0379067 | A1 | 12/2014 | Nguyen et al. |
| 2015/0182723 | A1 | 7/2015 | Leeflang et al. |
| 2015/0238178 | A1 | 8/2015 | Carroux |
| 2015/0265798 | A1 | 9/2015 | Nihonmatsu et al. |
| 2015/0320971 | A1 | 11/2015 | Leeflang et al. |
| 2016/0074067 | A1 | 3/2016 | Furnish et al. |
| 2016/0135840 | A1 | 5/2016 | Kick et al. |
| 2016/0213882 | A1 | 7/2016 | Fitterer et al. |
| 2016/0296332 | A1 | 10/2016 | Zhou et al. |
| 2016/0296730 | A1 | 10/2016 | Zhou et al. |
| 2017/0014157 | A1 | 1/2017 | Coyle et al. |
| 2017/0072163 | A1 | 3/2017 | Lim et al. |

(56) References Cited

U.S. PATENT DOCUMENTS

| | | |
|---|---|---|
| 2017/0209133 A1 | 7/2017 | Ciulla et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0229000 A1 | 8/2018 | Anderson et al. |
| 2018/0280137 A1 | 10/2018 | Nguyen et al. |

FOREIGN PATENT DOCUMENTS

| | | | |
|---|---|---|---|
| EP | 0249456 A2 | 12/1987 | |
| EP | 0385920 A2 | 9/1990 | |
| EP | 0592410 B1 | 10/1995 | |
| EP | 1139889 A1 | 10/2001 | |
| EP | 1694398 A2 | 8/2006 | |
| EP | 1793881 A2 | 6/2007 | |
| EP | 1804860 A2 | 7/2007 | |
| EP | 2101661 A1 | 9/2009 | |
| EP | 2288403 A2 | 3/2011 | |
| EP | 2475417 A2 | 7/2012 | |
| EP | 2862590 A1 | 4/2015 | |
| EP | 2911729 A1 | 9/2015 | |
| EP | 2995268 A1 | 3/2016 | |
| JP | 2012040145 A | 3/2012 | |
| WO | 9219312 A1 | 11/1992 | |
| WO | 9307812 A1 | 4/1993 | |
| WO | 03002181 A2 | 1/2003 | |
| WO | 2004002562 A2 | 1/2004 | |
| WO | 2004037333 A1 | 5/2004 | |
| WO | 2005018728 A2 | 3/2005 | |
| WO | 2007035471 A2 | 3/2007 | |
| WO | 2008002915 A2 | 1/2008 | |
| WO | 2008042311 A1 | 4/2008 | |
| WO | 2008147964 A1 | 12/2008 | |
| WO | 2009035745 A1 | 3/2009 | |
| WO | 2013044942 A1 | 4/2013 | |
| WO | 2014140093 A1 | 9/2014 | |
| WO | 2016164079 A1 | 10/2016 | |
| WO | 2017205456 A1 | 11/2017 | |
| WO | 2018054275 A1 | 3/2018 | |
| WO | WO-2018054275 A1 * | 3/2018 | ........... A61F 2/2427 |
| WO | 2018148488 A1 | 8/2018 | |

\* cited by examiner

METHODS OF MAKING AN EXPANDABLE SHEATH

CROSS-REFERENCE TO RELATED APPLICATIONS

This application claims the benefit of U.S. Provisional Application No. 62/702,993, filed Jul. 25, 2018, which is incorporated by reference in its entirety for all purposes.

FIELD

The present application is directed to a sheath for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as a prosthetic heart valve, at locations inside the body that are not readily accessible by surgery or where less invasive surgery is desirable. For example, aortic, mitral, tricuspid, and/or pulmonary prosthetic valves can be delivered to a treatment site using minimally invasive surgical techniques, including transcatheter delivery methods.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for the prosthetic implant, such as a heart valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths reduce the overall profile of the sheath to reduce risk of damage to the vessel. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque. The addition of radially expanding properties can also hinder a practitioner's ability to push the sheath without it bending or kinking. Thus, there remains a need for further improvements in introducer sheaths for endovascular systems used for implanting heart valves and other prosthetic devices.

Improved introducer sheaths are described in U.S. patent application Ser. No. 14/880,109, which is hereby incorporated by reference in its entirety. This sheath advantageously incorporates a longitudinal fold that can be unfolded to allow for radial expansion as an implant passes through. An outer, elastic tubular layer, surrounding the folded inner layer, can urge the expanded inner layer back to the folded configuration. Methods of making an inner layer with a longitudinal fold conventionally involve annealing operations to form the folded profile. The annealing operations are time consuming an require expensive heat shrink tube consumables. There are several thermal bonding operations that form the transition from folded low profile cross section to the large proximally located cross section that is required to mate with the hub/hemostasis valve housing. These operations add time, complexity, and incorporate potential failure locations at the bond joints.

SUMMARY

Disclosed herein are expandable introducer sheaths and methods of making and using the same. The sheaths are adapted to temporarily expand a portion of the sheath to allow for the passage of a delivery system for a cardiovascular device, then return to a non-expanded state after the passage of the system. The sheath includes an elongated annular member through which the cardiovascular device and its delivery system pass. In an embodiment, the annular inner member can be formed by coextruding a first and second material. The first material includes a fold, and the second material radially spaces the different parts of the fold from each other during fabrication and provides support for maintaining the tubular structure. The second material is removed once the coextrusion process is complete.

Disclosed herein is a method of making an expandable sheath. The method includes coextruding a first material and a second material. The first coextruded material defines an elongated annular member having a circumferentially extending thick wall portion. The thick wall portion has a first longitudinally extending end and a second longitudinally extending end. The second longitudinally extending end overlaps the first longitudinally extending end to create a folded overlapping segment. The thick wall portion of the annular member is integrally connected to a circumferentially extending thin wall portion. The thin wall portion extends between the first longitudinally extending end and the second longitudinally extending end of the thick wall portion. The first longitudinally extending end is radially closer to a central axis of the elongated annular member than the thin wall portion, and the second longitudinally extending end is radially farther from the central axis the thin wall portion.

The second coextruded material radially spaces the thin wall portion from the thick wall portion in during the coextrusion process. After the coextrusion is finished, the second coextruded material is then removed (by force, for example). The removal of the second extruded material allows for sliding movement of the first longitudinal end relative to the second longitudinal end and radial expansion of the elongated annular member. The second coextruded material can be removed by applying a force to at least one of the first and the second coextruded materials. The second coextruded material can be removed by applying a thermal treatment to at least one of the first and the second coextruded materials. The second coextruded material can be removed by applying a chemical treatment to at least one of the first and the second coextruded materials.

In some embodiments, the second coextruded material extends along the entire circumferential width of the overlapping segment. It can continue to extend circumferentially away from the overlapping segment. Two separate layers of the second coextruded material can be utilized. In some embodiments, a first layer of the second coextruded material is positioned between the first longitudinally extending end and the thin wall portion. In some embodiments, the first layer of the second coextruded material extends circumferentially away from the first longitudinally extending end. The first layer can extend circumferentially along an outer surface of the elongated annular member. A second layer of the second coextruded material is positioned between the second longitudinally extending end and the thin wall portion. The second layer of the second coextruded material can extend circumferentially away from the second longitudinally extending end. In some embodiments, the second layer of the second coextruded material extends circumferentially along an inner surface of the elongated annular member.

In some embodiments, the second coextruded material extends along an inner surface and an outer surface of the elongated member. The second coextruded material can extend around the entire circumference of the inner surface of the elongated member. The second coextruded material can also extend around the entire circumference of the outer surface of the elongated member.

In some embodiments of the method, a taper tube is coextruded near the proximal end of the annular member. The taper tube can have a diameter greater than a diameter of the elongated member. The taper tube is added as part of the coextrusion process, and therefore does not require the use of bonding processes (e.g., thermal bonding, chemical bonding, mechanical bonding). Finally, the annular member can be covered by an elastic outer layer which returns the annular member to a folded configuration after expansion (for example, after an implant passes through).

DESCRIPTION OF DRAWINGS

In the drawings, like reference numbers and designations in the various drawings indicate like elements.

DETAILED DESCRIPTION

Figure 1:
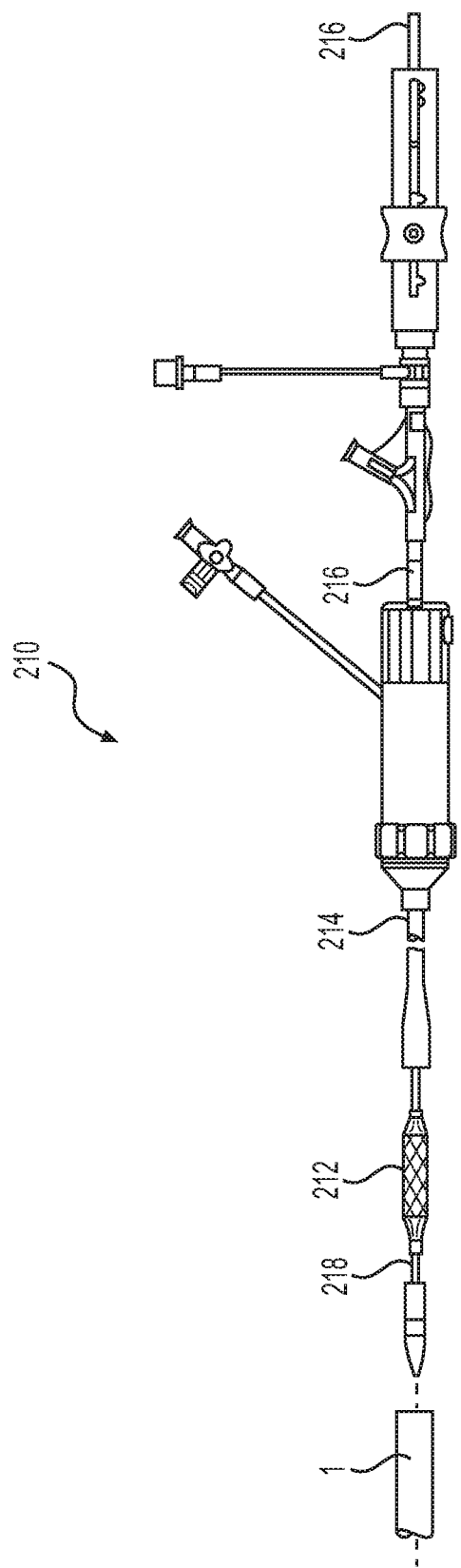
FIG. 1 is an elevation view of an expandable sheath along with an endovascular delivery system for implanting a prosthetic heart valve.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed herein are expandable introducer sheaths and methods of making and using the same. As will be described in further detail below, the expandable sheaths 1 are adapted to allow for temporary expansion of a portion of the sheath to accommodate the passage of a delivery system for a cardiovascular device, then return to a non-expanded state, or "recover" after the passage of the delivery system and device.

FIG. 1 illustrates a sheath 1 according to the present disclosure in use with a representative delivery apparatus 210 for delivering a prosthetic device 212, such as a tissue heart valve, to a patient. The apparatus 210 can include a steerable guide catheter 214 (also referred to as a flex catheter), a balloon catheter 216 extending through the guide catheter 214, and a nose catheter 218 extending through the balloon catheter 216. The guide catheter 214, the balloon catheter 216, and the nose catheter 218 in the illustrated embodiment are adapted to slide longitudinally relative to each other to facilitate delivery and positioning of the valve 212 at an implantation site in a patient's body, as described in detail below. Generally, a sheath 1 is inserted into a vessel, such as the transfemoral vessel, passing through the skin of patient, such that the distal end of the sheath 1 is inserted into the vessel. Sheath 1 can include a hemostasis valve at the opposite, proximal end of the sheath. The delivery apparatus 210 can be inserted into the sheath 1, and the prosthetic device 212 can then be delivered and implanted within patient.

The expandable introducer sheath 1 is adapted to allow for temporary radial expansion of a portion of the sheath to accommodate the passage of a delivery system for a cardiovascular device (e.g., prosthetic heart valve 212) and to then return to a non-expanded state after the passage of the delivery system with its prosthetic device. The expandable sheath 1 includes an elongated annular member 10 through which the delivery system and prosthetic heart valve 212 pass. As will be described in more detail below, the annular member 10 of the expandable sheath 1 can include longitudinally extending channels 12, 14 that facilitate the sheath's expansion for passage of the prosthetic heart valve 212. The channels 12, 14 are positioned such that upon expansion of the annular member 10 certain contact surfaces 22, 24 are brought into contact with adjacent surfaces of the delivery apparatus 210, thereby reducing friction between the annular member 10 and the passing structure. In some embodiments, the radial expansion of the expandable annular member 10 at any given portion along its length is due to the ability of base 20 and/or bridge members 30 of the annular member 10 to rotate. The rotation of these sections reduces the surface/contact area of the annular member 10 thereby reducing friction with the passing structure. The expandable sheath 1 can include an elastic outer layer 50. In some embodiments, the outer layer 50 can compress the annular member 10 towards a non-expanded configuration.

Figure 2A:
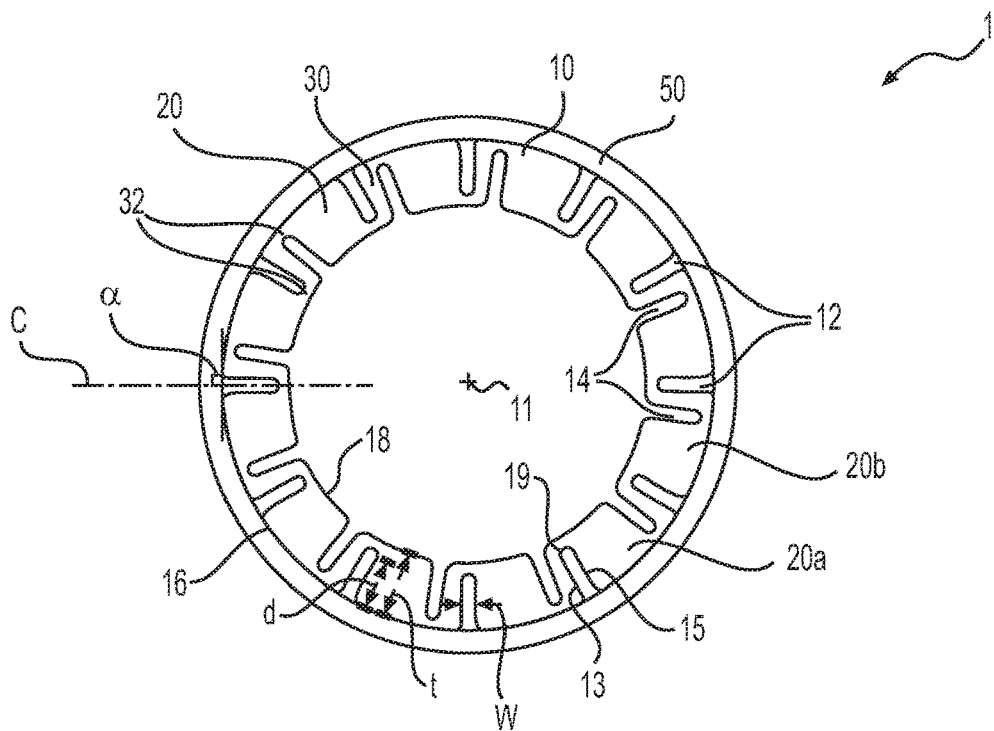
FIG. 2A shows a cross sectional view of an example expandable sheath in the non-expanded state.
Figure 2B:
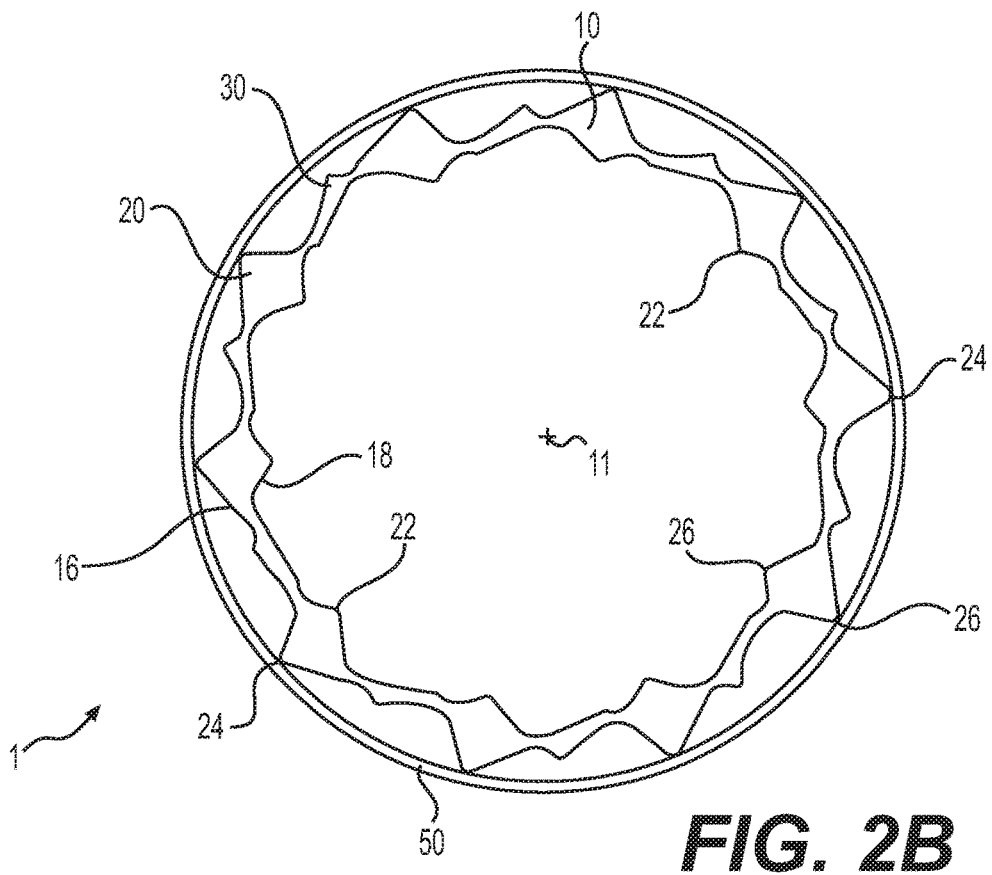
FIG. 2B shows the expandable sheath of FIG. 2A in the expanded state.

FIGS. 2A and 2B show a cross-section of an example expandable sheath 1 in an expanded (FIG. 2A) and a non-expanded (FIG. 2B) state. The non-expanded sheath 1 includes an inner annular member 10 and an outer layer 50. The outer layer 50 can be constructed from an elastic material that allows for temporary radial expansion of a portion of the outer layer 50 corresponding to the temporary radial expansion of the annular member 10 to accommodate the passage of the delivery system for a cardiovascular device (e.g., prosthetic heart valve 212). After passage of the delivery system with its prosthetic device, the annular member 10 and outer layer 50 return to a non-expanded state (FIG. 2B). As illustrated in FIG. 2A, the annular member 10 includes a plurality of base members 20 arranged around the circumference of the annular member 10 and bridge members 30 extending between opposing pairs of base members 20 (e.g., base member 20a and base member 20b). As illustrated in FIG. 2A, the base members 20 can define a rectilinear shape in cross-section. The base members 20 can include an outer edge that define the outer surface/diameter 16 of the annular member 10 and an inner edge that define the inner surface/diameter 18 when the annular member 10 is in a non-expanded state. Base members 20 can include side walls 15 that extend radially between the inner and outer edges. As illustrated in FIG. 2A, the outer edge has a longer length (around the circumference of the annular member 10) than the inner edge. The side walls 15 can meet the inner and outer edges at a curve (illustrated) or angle. The side walls 15 can terminate at the bridge member 30. As provided in FIG. 2A, the side walls 15 can meet the bridge members 30 at a curve. In other example annular members 10 (see e.g., FIG. 6A) the side wall of the base member 20 can meet the bridge member 30 at a straight or angled edge/joint. It is further contemplated that the base members 20 can define any regular or irregular shape in cross-section including, for example, square, rectangle, trapezoidal, circular, and oval. Likewise, bridge members 30 can define any regular or irregular shape. As provided in FIG. 2A, in the unexpanded state the bridge members 30 define a generally S-shape cross-section. That is, in cross-section, the bridge members 30 of FIG. 2A can include a relatively (radially) elongate shape that extends between bends (at joints 32) where the bridge member 30 couples to the adjacent base member 20. The bends bracket the ends of the elongate portion and serve as the connection to either the radially inward corner or radially outward corner of adjacent base members. The elongate portion of the bridge member 30 can also widen in the outward radial direction. As will be explained in more detail below, during expansion of the annular member 10 the shape of the base member 20 and/or bridge member 30 changes or otherwise deforms.

As illustrated in FIG. 2A, in the non-expanded state, the annular member 10 includes longitudinally extending channels 12, 14. Inward extending channels 12 extend radially inward from the outer surface/diameter 16 of the annular member 10 towards its longitudinal axis 11. The inward extending channels 12 are defined between a base member 20 and an adjacent bridge member 30. The outward extending channels 14 extend radially outward from the inner surface/diameter 18 of the annular member 10 in a radial direction away from the longitudinal axis 11 and are similarly defined between a base member 20 and an adjacent bridge member 30.

The inward and outward extending channels 12, 14 alternate in inward versus outward directionality, such that each channel of a selected set/direction is positioned circumferentially between two channels of the other set/direction (i.e., each inward extending channel 12 is positioned circumferentially between two outward extending channels 14, each outward extending channel 14 is positioned circumferentially between two inward extending channels 12).

As depicted in FIG. 2A, the inward and outward extending channels 12, 14 extend radially with respect to the longitudinal axis 11 of the annular member 10. For example, the centerline (c) of each of the inward and outward extending channels 12, 14 can create a 90-degree angle ($\alpha$) with a line tangent to the diameter of the annular member 10 proximate the opening of the channel.

The inward and outward extending channels 12, 14 extend a certain depth (d) into the wall thickness (t) of the annular member 10. For example, as illustrated in FIG. 2A, the inward and outward extending channels 12, 14 can have a depth (d) greater than 50% of the wall thickness (t) of the annular member 10. Though not illustrated, it is contemplated that the depth of the inward and outward extending channels 12, 14 can also vary around the circumference of the annular member 10.

The inward and outward extending channels 12, 14 can also define a width (w) measured along the length/depth of the channel. The width (w) can be defined between the sidewall of the corresponding bridge member 30 and base member 20, i.e., between side wall 13 and side wall 15. As illustrated in FIG. 2A, the width (w) of each channel can be uniform around the annular member 10. It is also contemplated that the width (w) of different channels can vary around the circumference of the annular member 10. The width (w) of the inward and outward extending channels 12, 14 can remain constant (see FIG. 2A) or vary along the depth (d) of the channel. For example, the width (w) of the channel can increase in a direction from the center of the annular member 10 towards the perimeter of the annular member 10.

The shape of the inward and outward extending channels 12, 14 can remain constant or vary around the circumference of the annular member 10. As depicted in FIG. 2A, each of the inward and outward extending channels 12, 14 have two substantially parallel and straight sides (defined by side wall 13 and side wall 15) that terminate at a rounded end 19. It is contemplated that the shape of inward and outward extending channels 12, 14 can define any regular or irregular shape and that the shape of each inward and outward extending channel 12, 14 can vary (or remain constant) around the circumference of the annular member 10.

In the embodiment shown in FIG. 2A, the inward and outward extending channels 12, 14 are evenly distributed around the circumference of the annular member 10 and are similar in size and shape. While it is contemplated that the size and spacing of the base members 20, bridge members 30 and corresponding inward and outward extending channels 12, 14 can vary, even spacing and uniform size and shape help to prevent tearing of the annular member 10 during expansion. For example, during expansion (shown in FIG. 2B) tension is distributed to many points around the circumference of the annular member 10 and not focused at a single location. This distribution of tension reduces the risk of tearing the annular member 10.

As described above, the annular member 10 and elastic outer layer 50 of the sheath 1 are designed to locally expand as the prosthetic device 212 is passed through the interior lumen of the sheath 1 and then substantially return to their original shape once the prosthetic device has passed through that portion of the sheath 1. That is, in the non-expanded state the outer diameter of the annular member 10 and outer layer 50 can be substantially constant across the length of the sheath 1 from the proximal end 3 to the distal end 5. As the prosthetic device 212 passes through the interior lumen of the sheath 1, the portion of the annular member 10 and outer layer 50 proximate the prosthetic device 212 expand radially, with the remaining length/portion of the annular member 10 and outer layer 50 in a substantially non-expanded state. Once the device has passed through a portion of the lumen of the sheath 1, that portion of the sheath 1 can substantially return to its original shape and size. FIG. 2B illustrates the annular member 10 and outer layer 50 in an expanded state. In the expanded state the outer diameters of the annular member 10 and elastic outer layer 50 are greater than the non-expanded diameters of the annular member 10 and outer layer 50.

To achieve expansion, the orientation of the base members 20 and bridge members 30 changes. As illustrated in FIG. 2B, the base members 20 rotate during expansion of the annular member 10. For example, the base members 20 rotate with respect to the central axis of each corresponding base member 20. Similarly, the bridge members 30 rotate and flex at joints 32 to extend in a direction around the circumference of the annular member 10, thereby increasing the circumferential distance/spacing between adjacent base members 20 and widening/changing the shape of each of the intervening inward and outward extending channels 12, 14. The bridge members 30 can be constructed from a flexible material to accommodate flexing at joints 32 and/or lengthening/deformation during expansion of the annular member 10 and then substantially return to the original, non-expanded shape/configuration. The base members 20 can be constructed from a same or different material than the bridge members 30. Accordingly, it is also contemplated that the base members 20 can flex and deform during expansion and contraction of the annular member 10.

As illustrated in FIG. 2B, in the expanded state the orientation of the base members 20 and bridge members 30 changes. Contact surfaces 22, 24 provided on the base members 20 now define the inner and outer diameters of the annular member 10, respectively. In the expanded state, the contact surfaces 24 define the inner diameter of the outer layer 50. The contact surfaces 22 extend towards the interior of the annular member 10 and reduce the contact surface area between the annular member 10 and the passing device, thereby lowering the coefficient of friction/resistance between the inner surface 18 of the annular member 10 and the passing device. The contact surfaces 22, 24 can define rounded/curved ends 26 or linear/angled ends 28 when viewed in cross-section. For example, the contact surfaces 22, 24 of the expanded embodiments shown in FIGS. 2B, 3B, 4B, 5B and 6C include rounded ends 26 in cross-section. In another example, the expanded annular member depicted in FIG. 7B includes both angled ends 28 and rounded ends 26 at the contact surfaces 22, 24. Referring back to FIG. 2B, the shape of the rounded ends 26, including the radii of curvature, can be constant across all base members 20 of the annular member 10. It is also contemplated that the shape of the rounded ends 26/contact surfaces 22, 24 may vary between base members 20, and vary between contact surface 22 and contact surface 24 of the same base member 20.

In transition back to the non-expanded state, the base members 20 and bridge members 30 move back to their original configuration/orientation. The transition back to the non-expanded state can be facilitated by the inclusion of an elastic outer layer 50 that extends over the elongated annular member 10. The outer layer 50 comprises a material having a lower elastic modulus than the annular member 10, which enables the outer layer 50 to force the annular member 10 back into the non-expanded state after passage of the cardiovascular device. The annular member 10 can be made of a more lubricious material than the outer layer 50. For example, the outer layer 50 can be made of, or incorporate, polyurethane, silicone, and/or rubber, and the annular member 10 can be made of, or incorporate, high density polyethylene, polytetrafluoroethylene, and/or other fluoropolymers.

Figure 3A:
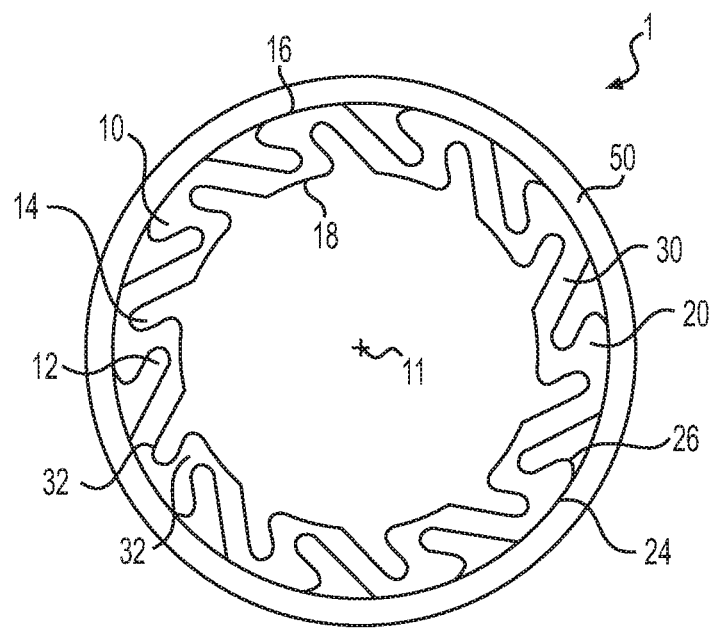
FIG. 3A shows a cross sectional view of an example expandable sheath in the non-expanded state.
Figure 3B:
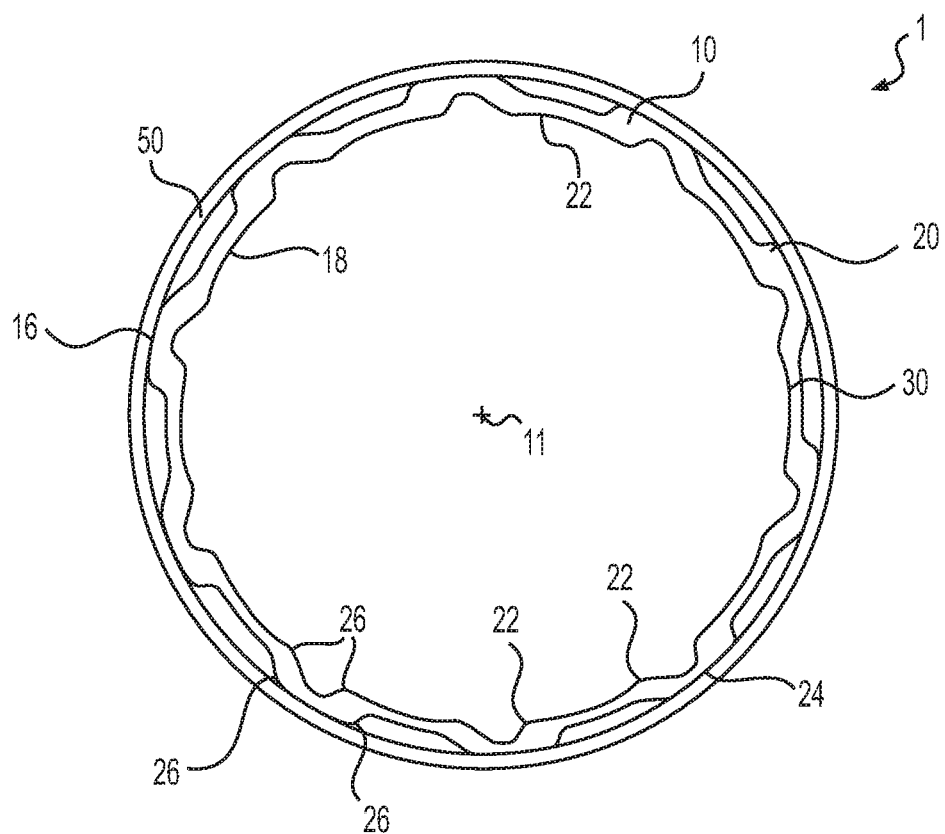
FIG. 3B shows the expandable sheath of FIG. 3A in the expanded state.

FIGS. 3A and 3B depict another example sheath 1 including an annular member 10 and elastic outer layer 50. The annular member 10 has a plurality of base members 20 arranged around the circumference of the annular member 10 and bridge members 30 extending between opposing pairs of base members 20. As illustrated in FIG. 3A, the base members 20 and bridge members 30 can define a curvilinear shape in cross-section. For example, as depicted in FIG. 3A, the base member 20 can define an elongated portion extending around the outer surface/diameter 16 of the annular member and terminating in a rounded end 26 contact surface 24, the elongated portion of the base member 20 defining the outer diameter of the annular member 10 in the non-expanded state. The bridge 30 can define an elongated member having substantially linear and parallel sides and terminating at a curved end proximate the inner surface/diameter 18 of the annular member 10, the curved end surface of the bridge 30 defining the inner diameter of the annular member 10 in the non-expanded state.

Similar to the annular member 10 depicted in FIG. 2A, in the non-expanded state the annular member 10 of FIG. 3A includes longitudinally extending channels 12, 14 defined between a bridge member 30 and adjacent base member 20 alternating in inward versus outward directionality around the circumference of the annular member 10. The inward extending channels 12 extend inward from the outer surface/diameter 16 of the annular member 10 and the outward extending channels 14 extend outward from the inner surface/diameter 18 of the annular member 10. The inward and outward extending channels 12, 14 can extend inward or outward from the inner/outer surface 16, 18 at an angle, e.g., at an angle other than 90-degrees (with respect to a line tangent to the diameter of the annular member 10 proximate the opening of the channel).

As described above, the annular member 10 and the elastic outer layer 50 of the sheath 1 are designed to locally expand in a radial direction between a non-expanded and an expanded state as the prosthetic device 212 is passed through the interior lumen of the sheath 1. FIG. 3B illustrates the annular member 10 and outer layer 50 in an expanded state. The orientation and/or shape of the base members 20 and bridge members 30 of the annular member 10 change during expansion. As illustrated in FIG. 3B, the base members 20 extend and elongate in a direction around the circumference of the annular member 10 when transitioned to the expanded state. The bridge members 30 change in orientation during expansion. In the non-expanded state the bridge members 30 extend is a direction toward/angled with respect to the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the annular member 10 and the outer layer 50.

As illustrated in FIG. 3B, in the expanded state the contact surfaces 22 provided on the base member 20 and/or bridge member 30 define the inner diameter of the annular member 10. Likewise, the contact surface 24 defines the outer diameter of the annular member 10, and the corresponding inner diameter of the outer layer 50 in the expanded state. The outside surface of the outer layer 50 defines the outermost diameter of the combined annular member 10/outer layer 50. Contact surfaces 22 reduce the contact surface area between the annular member 10 and the passing device, thereby lowering the coefficient of friction/resistance between the inner surface 18 and the passing device.

Figure 4A:
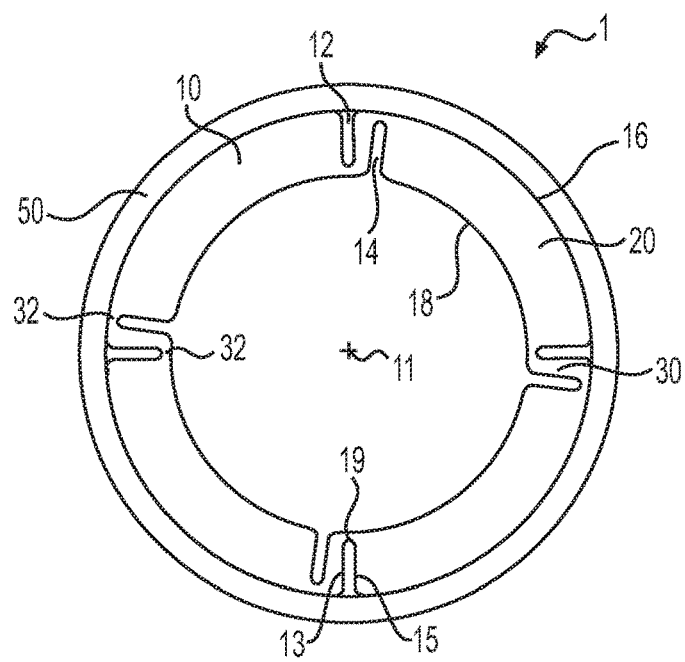
FIG. 4A shows a cross sectional view of an example expandable sheath in the non-expanded state.
Figure 4B:
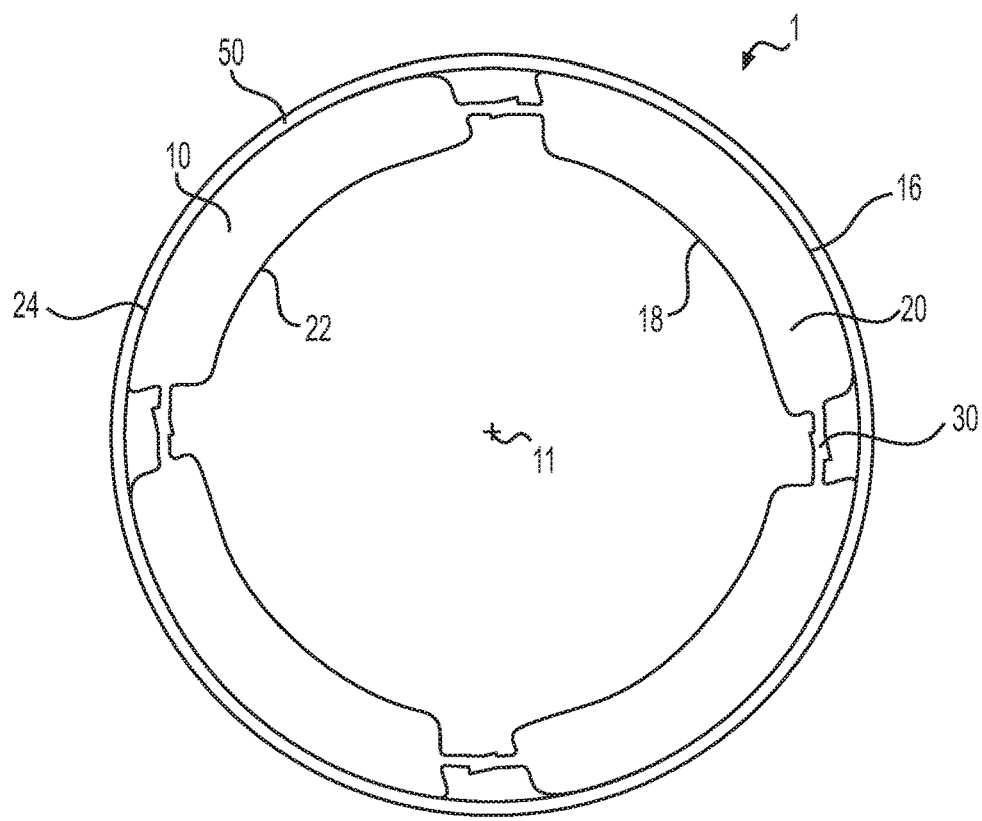
FIG. 4B shows the expandable sheath of FIG. 4A in the expanded state.

FIGS. 4A and 4B depict an example sheath 1 including an annular member 10 and elastic outer layer 50. The annular member 10 has four base members 20 arranged around the circumference of the annular member 10 and four corresponding bridge members 30 extending between opposing pairs of base members 20. In the non-expanded state, the base members 20 and bridge members 30 can define a curvilinear shape in cross-section. For example, as depicted in FIG. 4A, the base members 20 can define two arcuate portions having substantially similar shape terminating in two substantially linear portions extending in a radial direction with respect to the annular member 10. In the non-expanded state, the arcuate portions of the base members 20 define the inner and outer diameter of the annular member 10. In the non-expanded state, the bridge members 30 can define an S-shape in cross-section.

Similar to the annular member 10 depicted in FIGS. 2A and 3A, in the non-expanded state the annular member 10 of FIG. 4A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel.

As described above, the annular member 10 and the elastic outer layer 50 are designed to locally expand in a radial direction between a non-expanded and an expanded state as the prosthetic device 212 is passed through the interior lumen of the sheath 1. FIG. 4B illustrates the annular member 10 and outer layer 50 in an expanded state. The orientation and/or shape of the base members 20 and bridge members 30 of the annular member 10 change during expansion. As illustrated in FIG. 4B, the base members 20 extend and/or elongate in a direction around the circumference of the annular member 10 when transitioned to the expanded state. The bridge members 30 also change in orientation and/or shape during expansion. In the non-expanded state the bridge members 30 extend is a direction toward the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the sheath and the outer layer 50.

As illustrated in FIG. 4B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. It is contemplated that a portion of the inner surface 16 and outer surface 18 of the base member 20 can also define the inner and outer diameter of the annular member 10 in the expanded state. Contact surfaces 22 reduce the contact surface area between the annular member 10 and the passing device, thereby lowering the coefficient of friction/resistance between the annular member and the passing device.

Figure 5A:
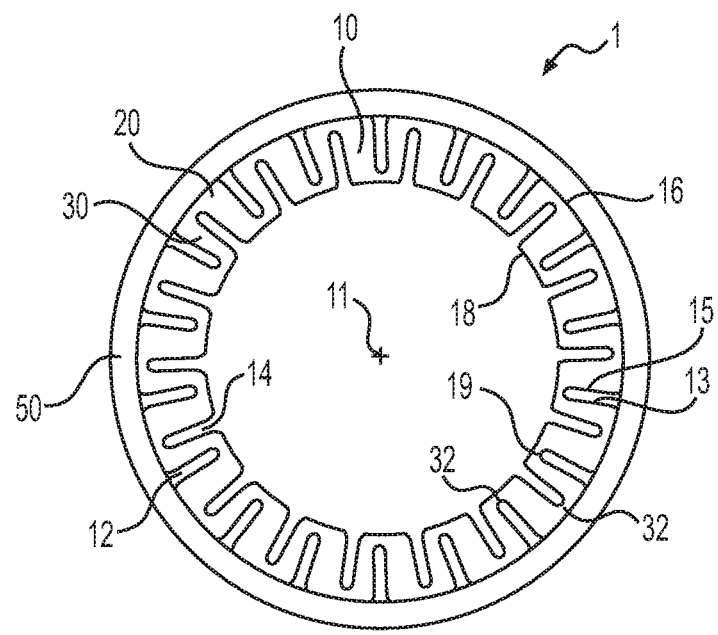
FIG. 5A shows a cross sectional view of an example expandable sheath in the non-expanded state.
Figure 5B:
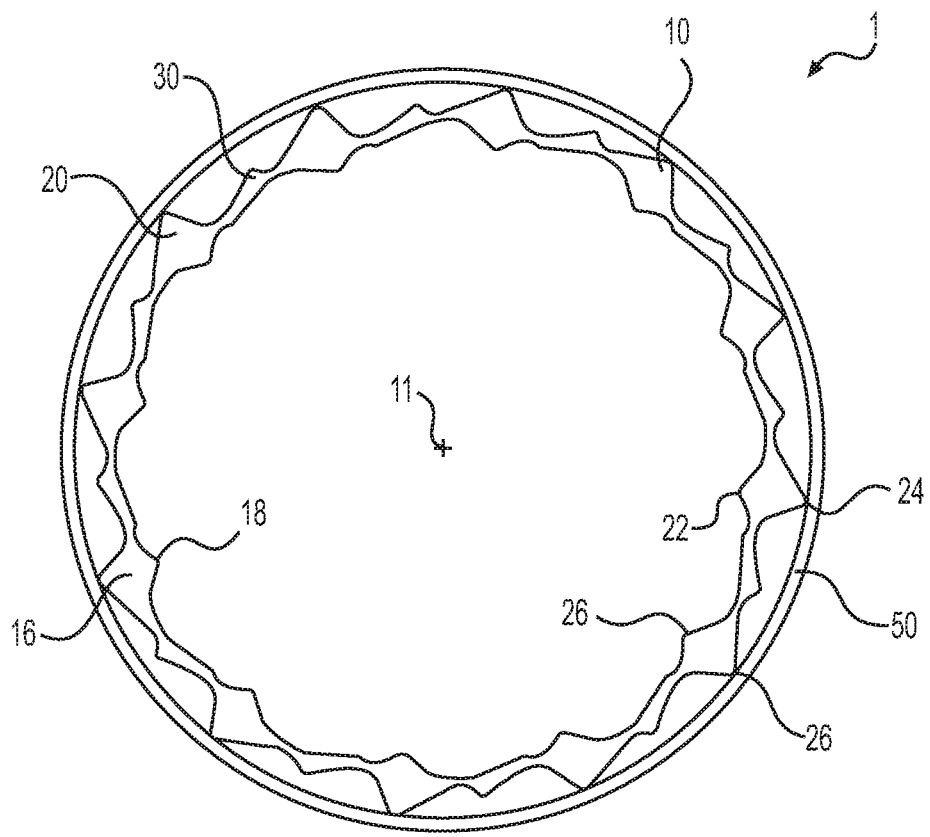
FIG. 5B shows the expandable sheath of FIG. 5A in the expanded state.

FIGS. 5A and 5B depict another example sheath 1 including an annular member 10 and elastic outer layer 50. The annular member 10 has eighteen base members 20 arranged around the circumference of the annular member 10 and eighteen corresponding bridge members 30 extending between opposing pairs of base members 20. In the non-expanded state, the base members 20 and bridge members 30 can define a curvilinear shape in cross-section. For example, as depicted in FIG. 5A, the base members 20 can define a semi-rectangular shape. The bridge members 30 can define an S-shape in cross-section.

Similar to the annular members 10 depicted in FIGS. 2A, 3A and 4A, in the non-expanded state the annular member 10 of FIG. 5A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel.

As described above, the annular member 10 and the elastic outer layer 50 are designed to locally expand in a radial direction between a non-expanded and an expanded state as the prosthetic device 212 is passed through the inner lumen of the sheath 1. FIG. 5B illustrates the annular member 10 and outer layer 50 in an expanded state. The orientation and/or shape of the base members 20 and bridge members 30 of the annular member 10 change during expansion. As illustrated in FIG. 5B, the base members 20 extend and/or elongate in a direction around the circumference of the annular member 10 when transitioned to the expanded state. The bridge members 30 also change in orientation and/or shape during expansion. In the non-expanded state the bridge members 30 extend in a direction toward the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the annular member 10 and the outer layer 50.

As illustrated in FIG. 5B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. Contact surfaces 22 reduce the contact surface area between the annular member 10 and the passing device, thereby lowering the coefficient of friction/resistance between the annular member and the passing device.

Figure 6A:
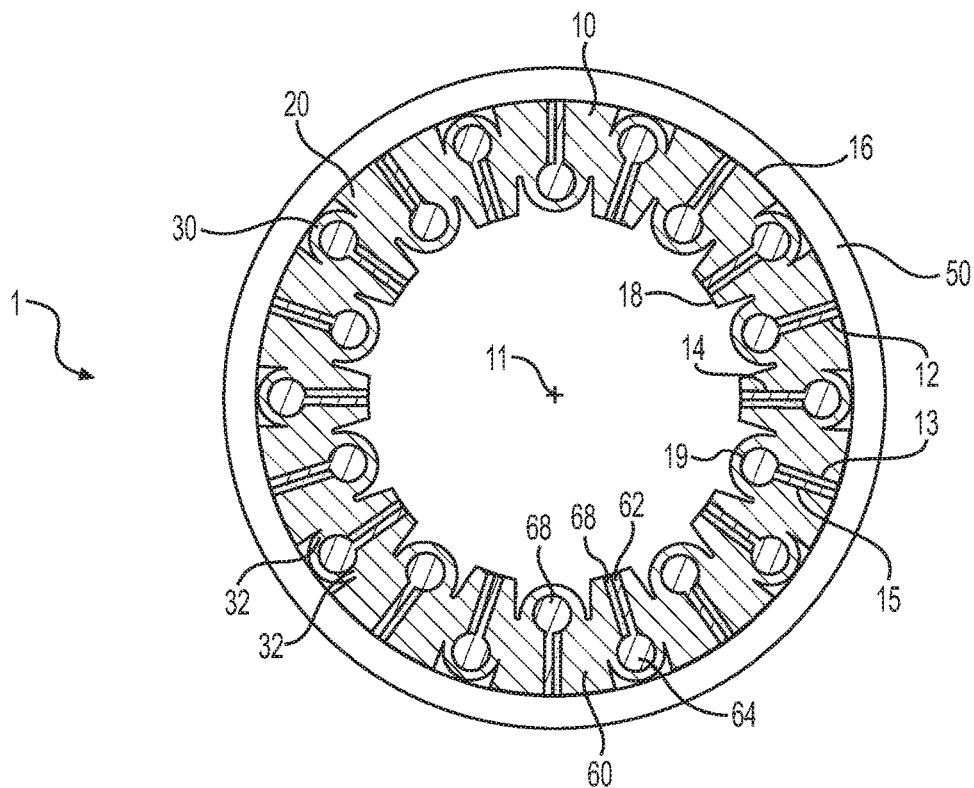
FIG. 6A shows a cross sectional view of an example an expandable sheath in the non-expanded state.
Figure 6B:
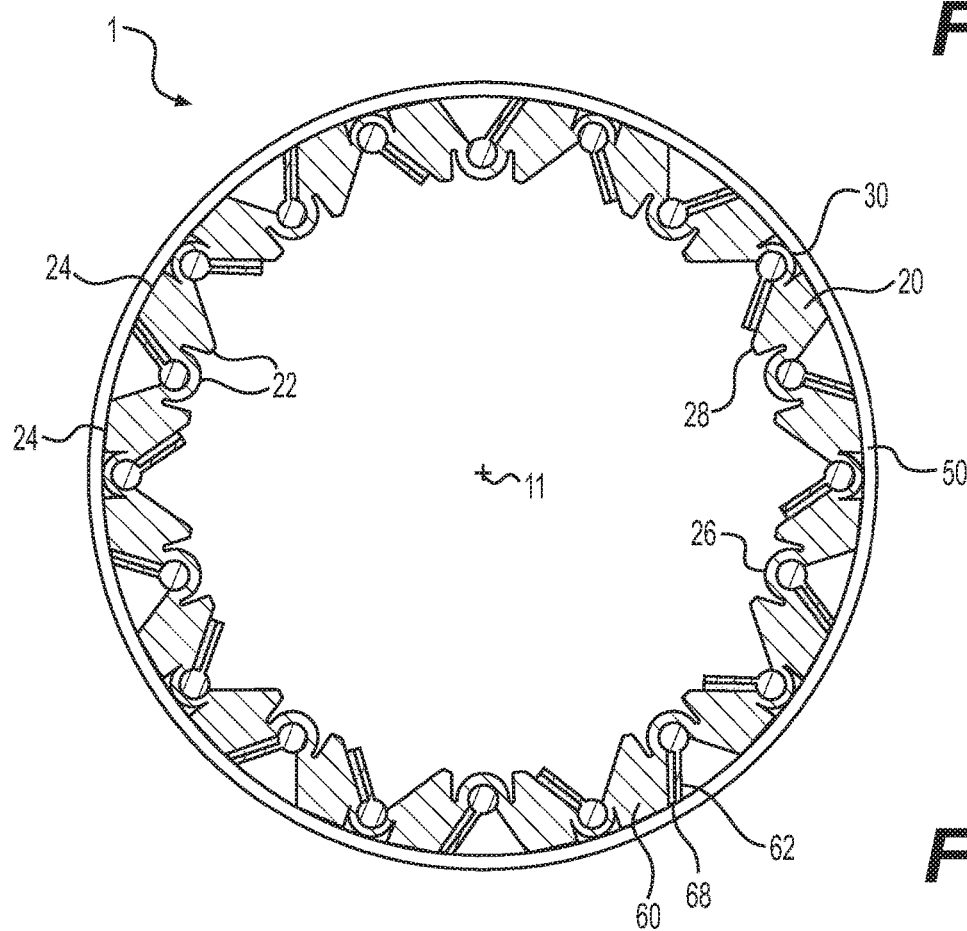
FIG. 6B shows the expandable sheath of FIG. 6A in the expanded state.

FIGS. 6A and 6B depict another example sheath 1 including an annular member 10 and elastic outer layer 50. The annular member 10 has base members 20 arranged around the circumference of the annular member 10 and corresponding bridge members 30 extending between opposing pairs of base members 20.

In the non-expanded state, the base members 20 and bridge members 30 can define a curvilinear shape in cross-section. For example, as depicted in FIG. 6A, the base members 20 define a wedge shape. The bridge members 30 define an arcuate/curved shape in cross-section.

Similar to the annular members 10 depicted in FIGS. 2A, 3A, 4A and 5A, in the non-expanded state the annular member 10 of FIG. 6A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel. The shape, in cross-section, of the inward and outward extending channels 12, 14 as depicted in FIG. 6A can include two substantially parallel and straight sides (defined by side wall 13 and side wall 15) that terminate at a rounded end 19. The rounded end 19 can have a width/diameter greater than the width (w) of the corresponding inward and outward extending channels 12, 14.

As described above, the annular member 10 and the elastic outer layer 50 of the sheath 1 are designed to locally expand in a radial direction between a non-expanded and an expanded state as the prosthetic device 112 is passed through the interior lumen of the sheath 1. FIG. 6B illustrates the annular member 10 and outer layer 50 in an expanded state. The orientation and/or shape of the base members 20 and bridge members 30 of the annular member 10 change during expansion. As illustrated in FIG. 6B, the base members 20 rotate, extend and/or elongate in a direction around the circumference of the annular member 10 when transitioned to the expanded state. For example, the base members 20 can rotate with respect to the central axis of each corresponding base member 20. Similarly, the bridge members 30 also change in orientation and/or shape during expansion. In the non-expanded state the bridge members 30 define an arcuate shape that flexes to increase in radius/length upon expansion of the annular member 10. It is also contemplated that the bridge members 30 can rotate, elongate and/or extend in a direction around the circumference of the annular member 10 upon expansion. Upon expansion of the annular member 10, the distance/spacing between adjacent base members 20 increases, widening and changing the shape of the intervening inward and outward extending channels 12, 14 and increasing the overall diameter of the annular member 10 and the outer layer 50. The wall thickness of the annular member 10 is thinner at the bridge members 30 than compared to the base members 20. The decreased thickness at the bridge members 30 eases the bending of the bridge members 30 during expansion, lessening the chance of fracture.

As illustrated in FIG. 6B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. Contact surfaces 22 reduce the contact surface area between the annular member 10 and the passing device, thereby lowering the coefficient of friction/resistance between the annular member and the passing device.

As illustrated in FIGS. 2A, 3A, 4A, 5A, 6A and 7A, the size, shape, spacing and number of channels can vary. For example, the non-expanded embodiments of FIGS. 2A and FIG. 7B have twenty four combined inward and outward extending channels 12, 14. The non-expanded embodiments of FIG. 3A and FIG. 6A have twenty combined inward and outward extending channels 12, 14, the non-expanded embodiment of FIG. 4A has eight combined inward and outward extending channels 12, 14, and the non-expanded embodiment of FIG. 5A has thirty six combined inward and outward extending channels 12, 14.

Sheaths of the present disclosure can be used with various methods of introducing a prosthetic device into a patient's vasculature. Generally, during use, the expandable sheath 1 is passed through the skin of patient (usually over a guidewire) such that the distal end region of the expandable sheath 1 is inserted into a vessel, such as a femoral artery, and then advanced to a wider vessel, such as the abdominal aorta. The delivery apparatus 210 is then inserted through the expandable sheath 1. The prosthetic device is then delivered to the implantation site and implanted within the patient. During the advance of the prosthetic device through the expandable sheath 1, the device and its delivery system exerts a radially outwardly directed force on the portion of the annular member 10, the annular member 10 exerts a corresponding radially outwardly directed force on the outer layer 50, causing both the annular member 10 and the outer layer 50 to expand locally to accommodate the profile of the device. The expansion of the annular member 10 widens the longitudinally extending channels 12, 14 of the annular member and causes the movement of longitudinally extending contact surfaces 22, 24 toward the inner and outer surfaces 16, 18 of the annular member 10.

As the prosthetic device and its delivery system passes through the expandable sheath 1, the expandable sheath 1 recovers. That is, it returns to its original, non-expanded configuration. In some embodiments, this is facilitated by outer layer 50, which has a lower elastic modulus than annular member 10. The outer layer 50 moves the contact surfaces 22, 24 of the annular member 10 away from the inner and outer surfaces after the passage of the prosthetic valve 212.

As described above, the expandable sheath 1 can be used to deliver, remove, repair, and/or replace a prosthetic device. In one example, the expandable sheath 1 described above can be used to deliver a tissue heart valve to a patient. For example, a tissue heart valve (in a crimped state) can be placed on the distal end portion of an elongated delivery apparatus and inserted into the sheath. Next, the delivery apparatus and crimped heart valve can be advanced through the patient's vasculature to the treatment site, where the valve is implanted.

Beyond transcatheter heart valves, the expandable sheath 1 can be useful for other types of minimally invasive surgery, such as any surgery requiring introduction of an apparatus into a subject's vessel. For example, the expandable sheath 1 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Figure 7A:
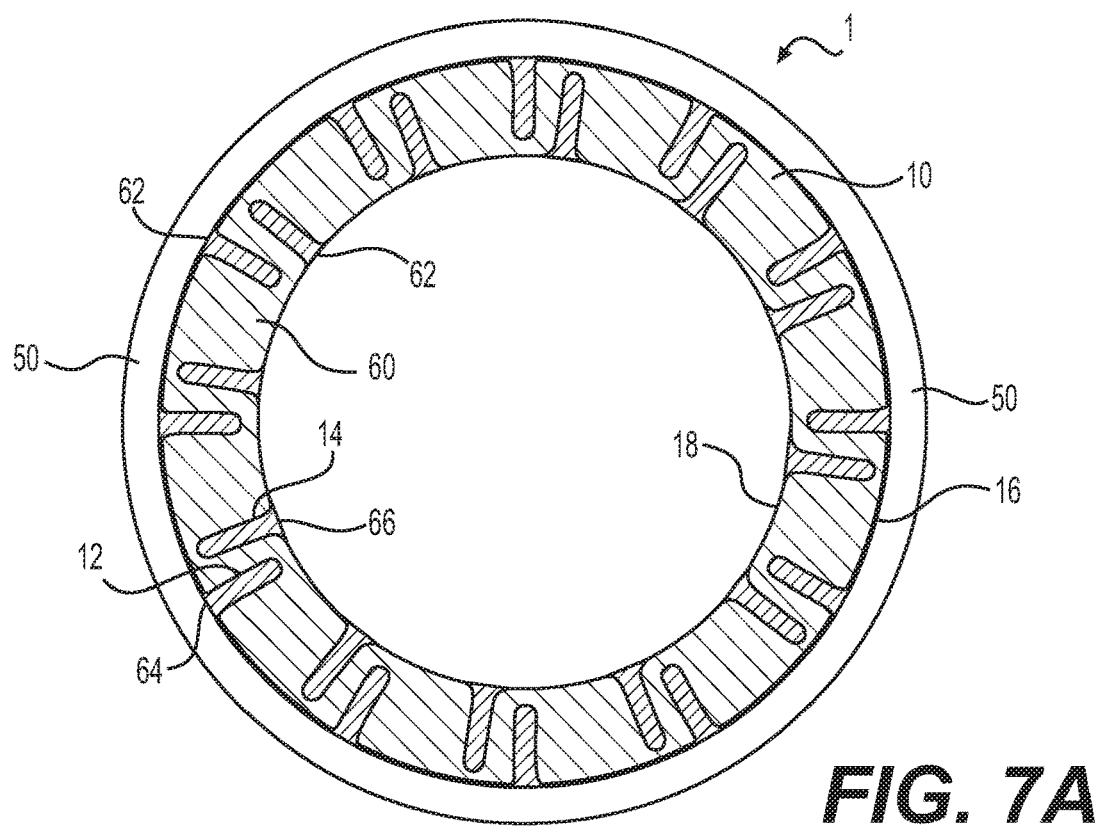
FIG. 7A shows a cross sectional view of an example expandable sheath during an intermediate processing step.
Figure 7B:
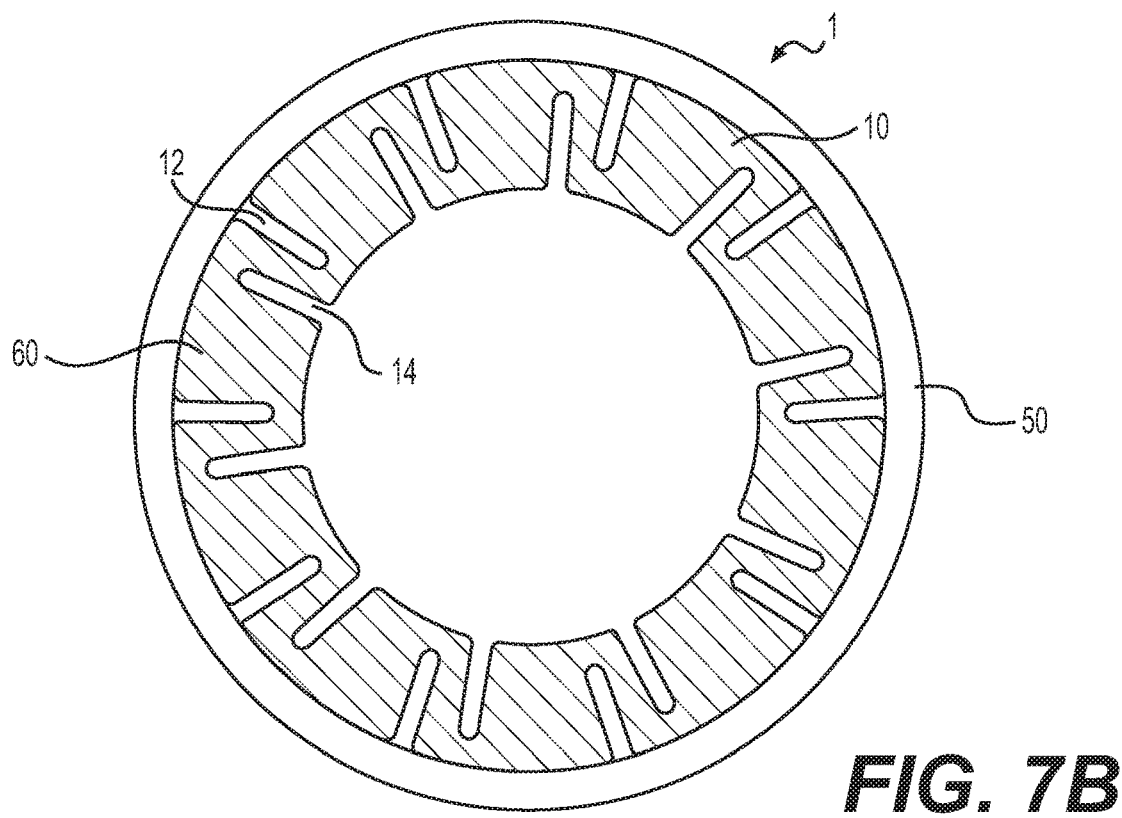
FIG. 7B shows the expandable sheath of FIG. 7A in a non-expanded state, after removal of a sacrificial material.
Figure 7C:
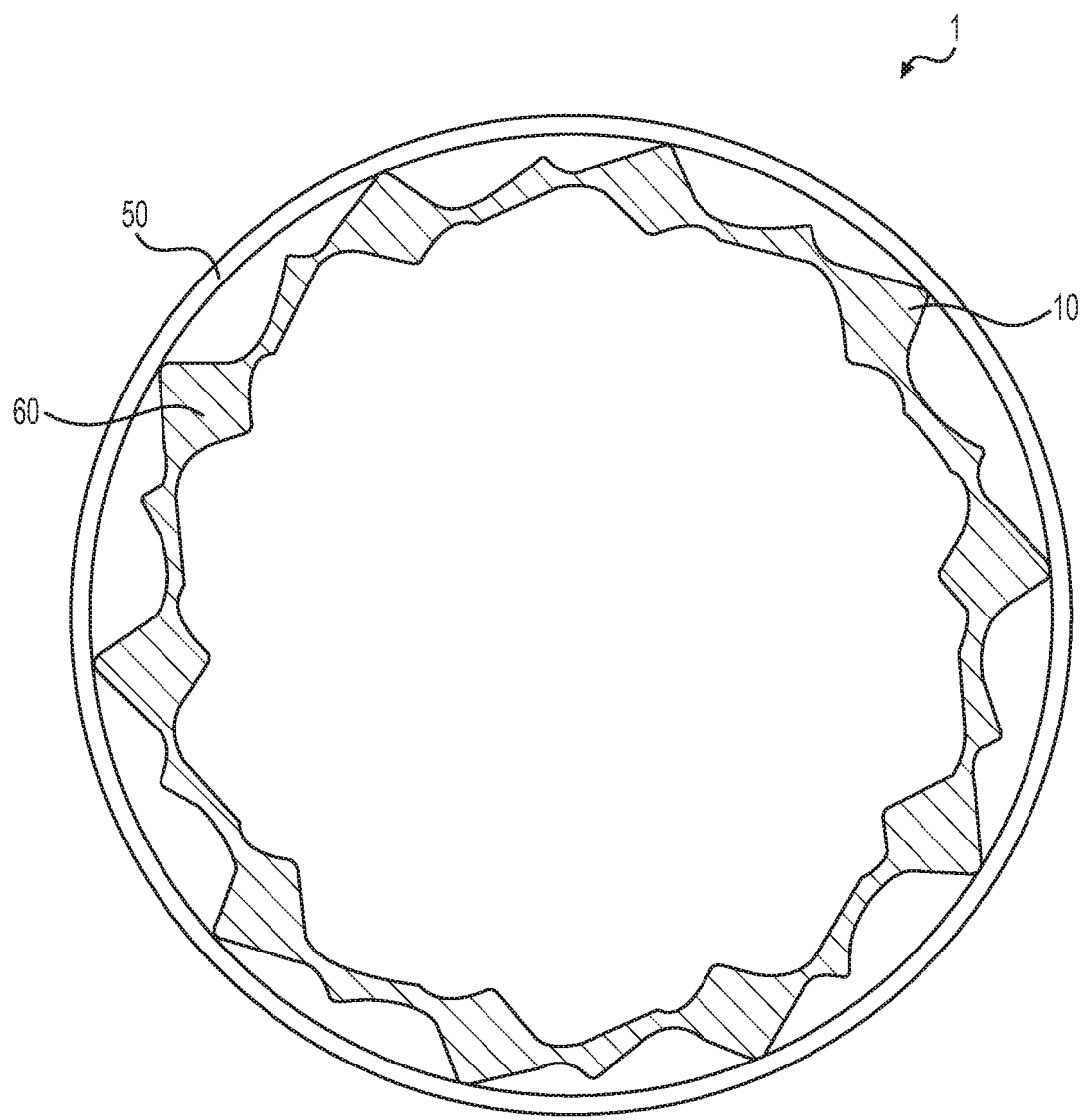
FIG. 7C shows the expandable sheath of FIG. 7B in the expanded state.

FIGS. 7A-7C show cross-sections of an expandable sheath 1 including an annular member 10 and outer layer 50 similar to the annular member 10 and outer layer 50 depicted in FIGS. 2A and 2B. FIG. 7A shows a cross-sections of an expandable sheath 1 during an intermediate processing step that includes a second material in addition to the material used to form the annular member 10. During processing, a tube is coextruded containing a first material 60 and a second material 62. The first material 60 defines the annular member 10 discussed above. The second material 62 does not adhere to the first material 60 and defines a first and second set of longitudinally extending ribbons 64, 66. The second material 62 could be, or could incorporate, nylon, polyethylene terephthalate, and/or polybutylene terephthalate, for example. The first and second set of ribbons 64, 66 form the inward and outward extending channels 12, 14 of the annular member 10 during the extrusion process. The first set of ribbons 64 extends inwardly from the outer surface 16 toward the inner surface 18 of the annular member 10, and the second set of ribbons 66 extends outwardly from the inner surface 18 toward the outer surface 16 of the annular member 10. Each ribbon of a selected set is positioned circumferentially between two ribbons of the other set.

In some embodiments, the second material 62 is a sacrificial material. For example, the ribbons 64, 66 of the second material 62 shown in FIG. 7A are removed after coextrusion, exposing the longitudinally extending channels 12, 14 described above and as shown in the non-expanded embodiment of FIG. 7B.

However, some embodiments, such as the one shown in FIG. 6A, the first material 60 and second material 62 of the annular member 10 are coextruded with a third material 68. This third material 68 is in contact with a portion of the first material 60 and a portion of the second material 62, and adheres to both the first and second materials 60, 62. Because of the adherent third material 68, the second material 62 is not removed. However, it still does not adhere to first material 60. Instead, the third material 68 acts as a tie layer to hold the first and second materials 60, 62 together during expansion of the annular member 10. This eliminates the need to remove the ribbons 64, 66 of the second material 62 prior to use, while still allowing a widening of a channel between the non-adherent first 60 and second 62 materials during the expansion of the annular member 10. The retention of the second material 62 also increases the torque of the finished sheath, so that a user finds it easier to twist the sheath.

Some methods include a step of covering the annular member 10 with the outer layer 50 after coextrusion. As discussed above, the outer layer 50 is formed of, or incorporates, a material with a lower elastic modulus than the annular member 10.

Figure 8:
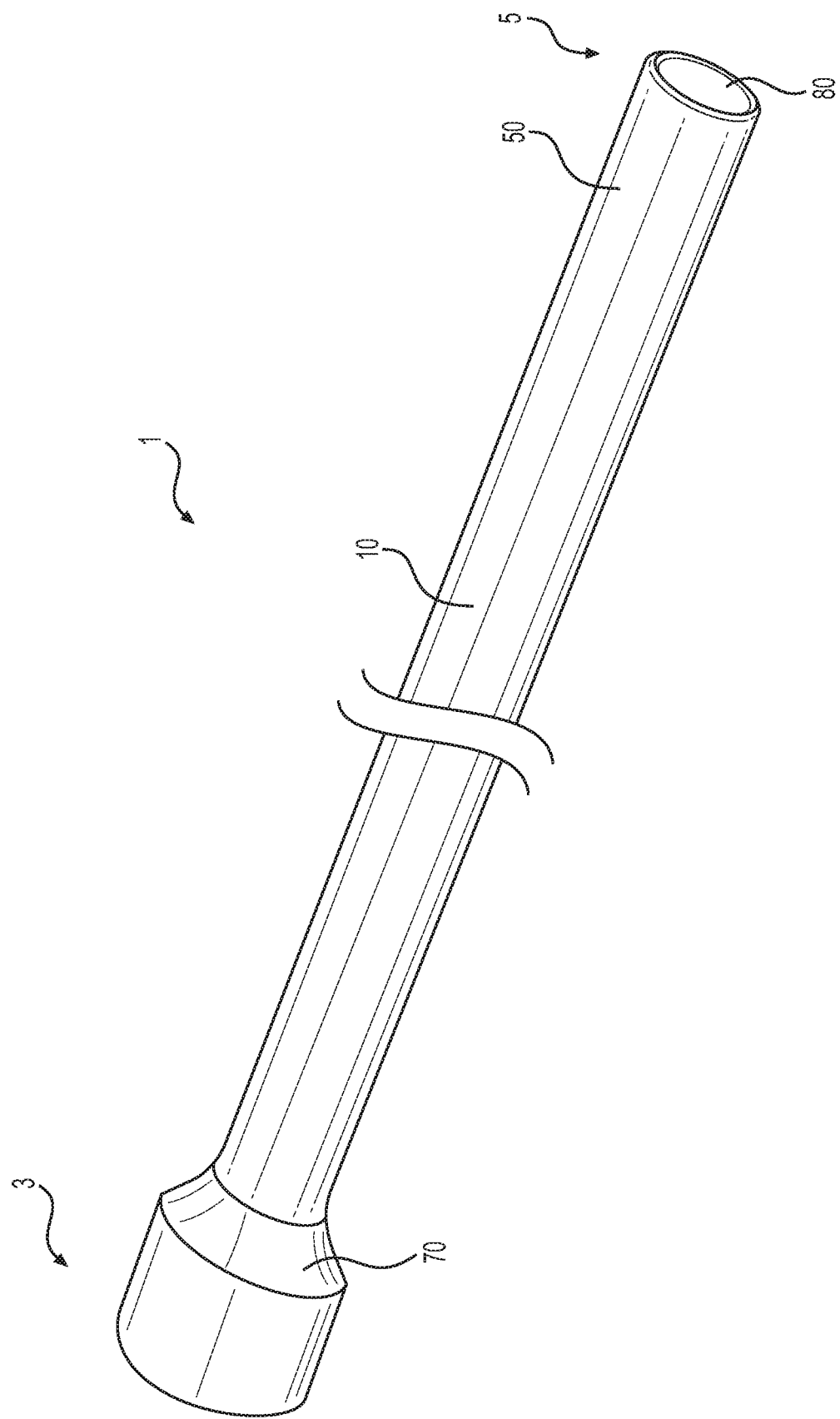
FIG. 8 shows a perspective view of an expandable sheath.

FIG. 8 shows a perspective view of an example sheath 1. In this view, only the outer layer 50 is visible. The sheath 1 comprises a proximal end 3 and distal end 5 opposite the proximal end 3. The sheath 1 can comprise a hemostasis valve inside the lumen of the sheath 1, at or near the proximal end 3. The sheath 1 can include a taper tube 70, a flared proximal end. In some embodiments of the method of making, the taper tube 70 is added to the coextrusion. The addition of the second material 62 will stabilize the coextrusion process and make it possible to add a taper tube 70 during extrusion. This is advantageous because it makes it possible to eliminate the typical taper tube manufacturing steps of flaring (increasing the inner diameter of the sheath) and bonding (increasing the wall thickness after flaring).

Additionally, the sheath 1 can comprise a soft distal tip 80 at the distal end 5. The soft tip 80 can be provided with a lower hardness than the other portions of the sheath 1. In addition to the method of making the expandable sheath described above, a method of making a distal tip 80 of an expandable sheath 1 is demonstrated in the flow chart of FIG. 9. The distal tip 80 can be formed on the annular member 10, outer layer 50, or on the annular member 10 and outer layer 50 combined. The distal tip 80 of the expandable sheath 1 is softer and more elastic than the more proximal regions of the expandable sheath 1 because it must give easily when encountering tissue to reduce the possibility of injury and it must retain the ability to expand after the sealing (reflowing) process wherein the distal tip 80 is sealed to prevent blood from entering the space between the annular member 10 and the outer layer 50. A first step to making the distal tip 80 is to attach a separate distal tube 82 to the distal end 5 of the expandable sheath 1, for example, by reflowing the materials together. Alternatively, the distal tube 82 can be added to the distal end 5 of the sheath 1 via specialized extrusion technology. The distal tube 82 is formed of, or incorporates, a material having greater elasticity than the remainder of the expandable sheath 1. One example material is Pebax.

Next, a portion of the distal tube 82 is pinched to create a longitudinally extending outer crease 84. The pinched portion is folded over an outer surface of the distal tube 82 in a circumferential direction, creating a longitudinally extending flap 86 that is bounded by the outer crease 84 and a longitudinally extending inner crease 85. The inner crease 85 of the flap 86 is cut in a longitudinal direction from the distal edge 83 of the distal tube 82 to a proximally spaced point along the longitudinal axis of the distal tube 82. This creates a longitudinally extending inner edge 87. The flap 86 is cut circumferentially from the outer crease 84 to the inner crease 85 at the proximally spaced point, such that the longitudinal cut of the inner crease 85 meets the circumferential cut at the proximally spaced point. The inner edge 87 of the flap is then extended in a circumferential direction around the outer surface 81 of the distal tube 82 and adhered to the outer surface 81.

Figure 9:
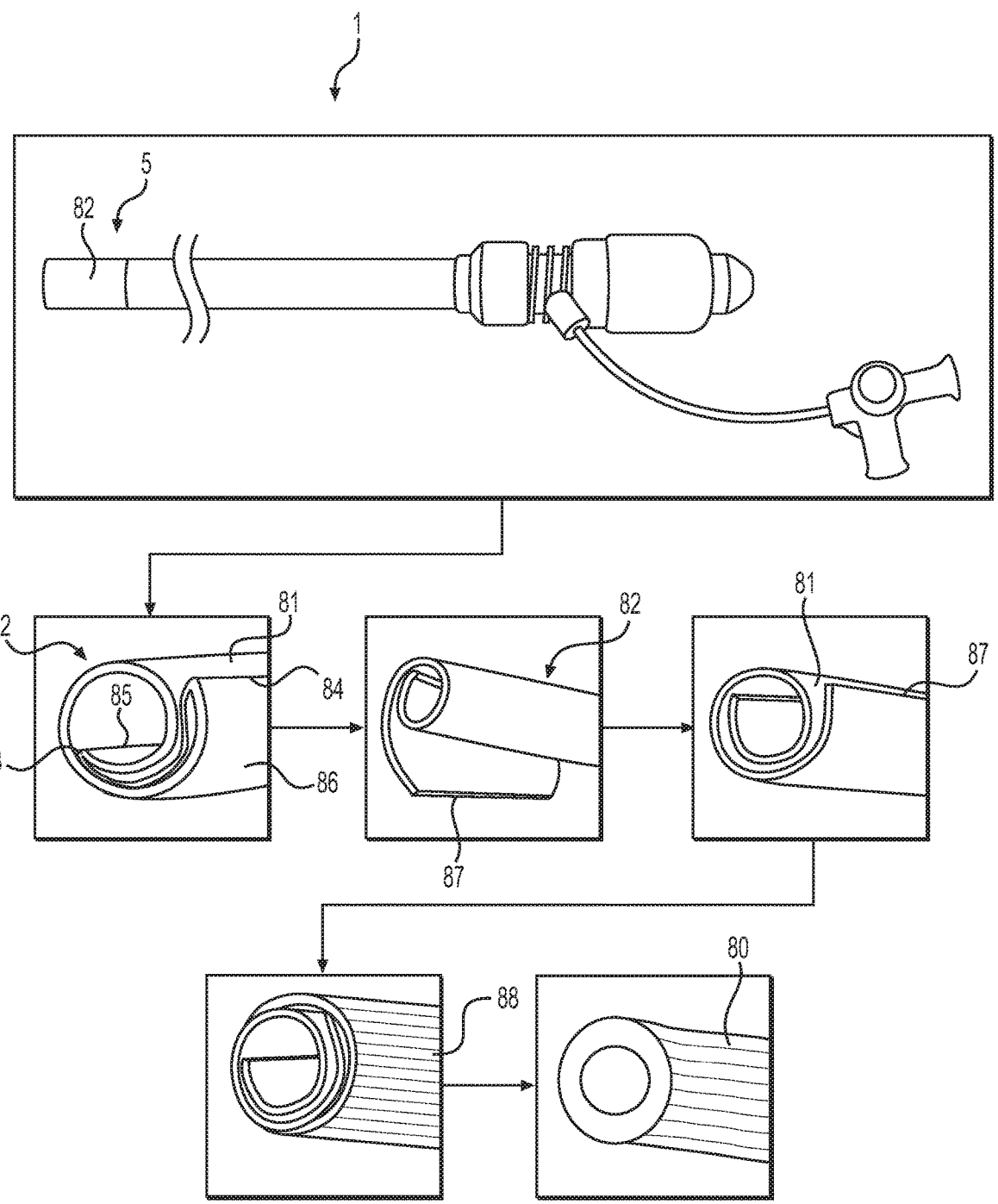
FIG. 9 shows a method of making a distal tip of an expandable sheath.

In some embodiments, such as the one shown in FIG. 9, adhering the inner edge 87 of the flap 86 to the outer surface 81 can include covering the distal end with an outer jacket 88, then reflowing the outer jacket 88 with the distal tube 82 to form a sealed distal end. The outer jacket 88 is also formed of highly elastic materials. One example material is Neusoft. This outer jacket 88 can, in some embodiments, be the same layer as the outer layer 50 shown in FIGS. 2A-B. Because the flap 86 is unfolded and wrapped around the outer surface 81 before reflowing, the final wall thickness of the resulting distal tip varies minimally around its circumference.

Figure 10:
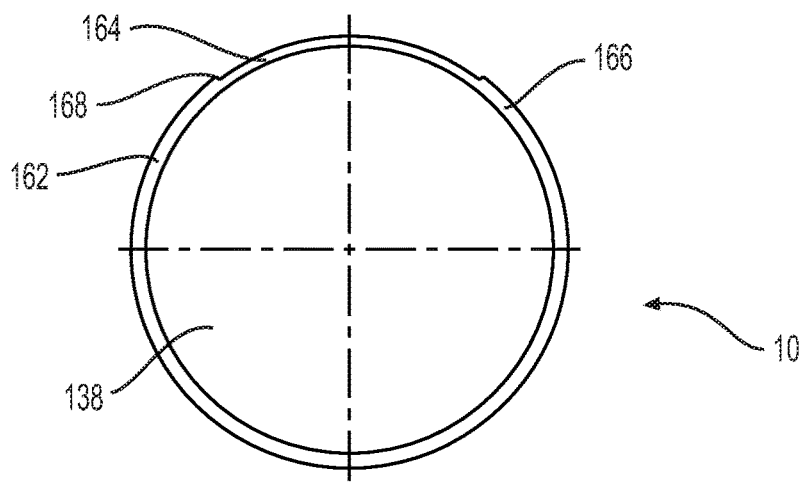
FIG. 10 is a cross sectional view of an embodiment of the inner tubular layer of an example sheath in the expanded state.

FIG. 10 shows an embodiment of an annular member 10 in a radially expanded state. The annular member 10 has a thick wall portion 162 integrally formed and coextruded with a thin wall portion 164. The annular member 10 shown in FIG. 10 is preferably constructed of a relatively stiff material (as compared to the outer layer 50) such as a stiff polymer like high density polyethylene (HDPE) or an equivalent polymer. Integral construction, such as integral extrusion, of the thick and thin wall portions 162, 164 advantageously avoids the leakage present in some conventional sheaths that use a split in the sheath to promote expandability. Other conventional sheaths tend to leak close to the proximal end where the sheath is stretched the most during passage of the prosthetic device. Also, integral construction improves the ability to torque the sheath 1.

The thick wall portion 162 of the annular member 10, as in the illustrated embodiment of FIG. 10, has a C-shaped cross section with a first longitudinally extending end 166 and a second longitudinally extending end 168. The first and second ends 166, 168 define those portions of the annular member 10 where the thickness of the thick wall portion 162 starts to narrow or otherwise transition to the thin wall portion 164 on the cross-section. That transition extends longitudinally in the direction of the longitudinal axis of the sheath 1, such that the thick wall portion 162 forms an elongate C-shaped channel.

The thin wall portion 164 extends between the first and second ends 166, 168 of the thick wall portion 162 which together define the tubular shape of the annular member 10. Central lumen 138 extends longitudinally within that tubular shape. FIG. 10, in particular, shows the central lumen 138 in its expanded diameter which is larger than the initial diameter of the elastic outer layer 50.

Figure 11:
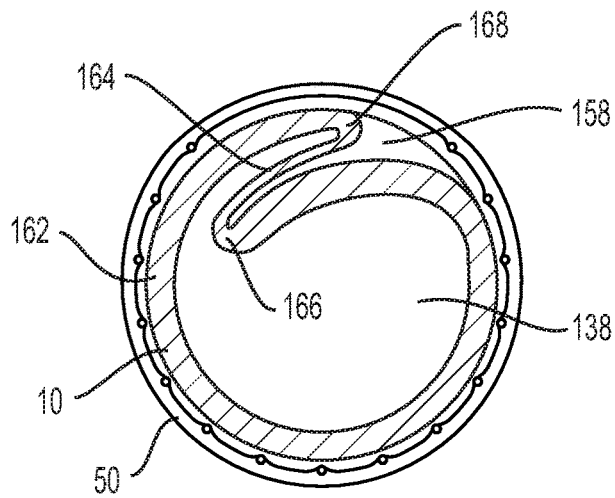
FIG. 11 is a cross sectional view of both the inner and outer tubular layers of the example sheath of FIG. 10. In this example, the inner tubular layer is in the compressed condition.
Figure 12:
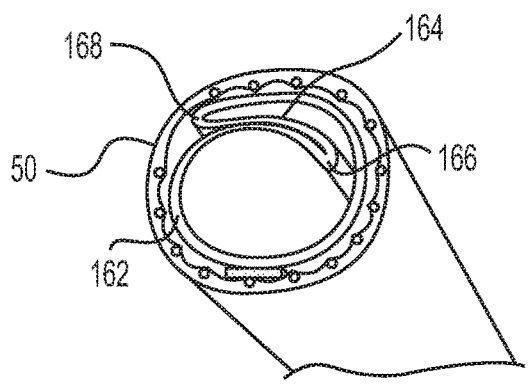
FIG. 12 is a perspective view of the distal end of the example sheath of FIG. 10.

FIGS. 11 and 12 show the annular member 10 in its non-expanded, compressed or folded condition, such that the annular member 10 folded up and fit into the initial elastic lumen 158 of the elastic outer layer 50. In the compressed condition, the elastic outer layer 50 urges the first longitudinally extending end 166 under the second longitudinally extending end 168 of the annular member 10. As illustrated in FIGS. 11 and 12, compression and folding of the annular member 10 positions/layers the thin wall portion 164 between the first and second longitudinally extending ends 166, 168 and the overlapping sections of the thick wall portion 162.

As will be described in more detail below, the foldable annular member 10 shown in FIGS. 10-12 can be formed by a coextrusion process wherein the annular member 10 is coextruded with a second, sacrificial, material while the annular member 10 is in a folded state. The second material is then removed, as described above, leaving behind the folded annular member 10.

Figure 13:
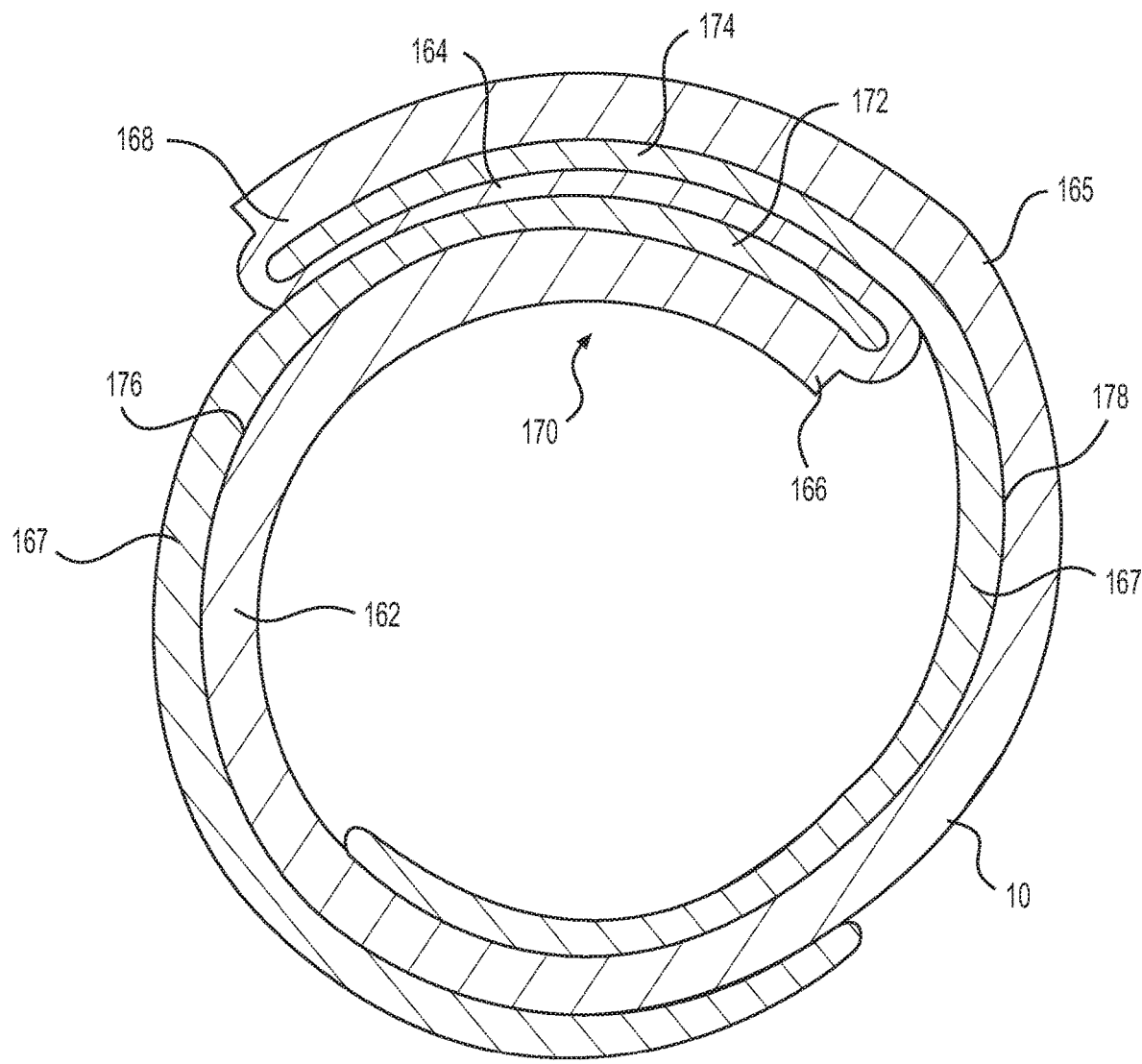
FIG. 13 is a cross sectional view of the inner tubular layer of FIG. 10 during an intermediate processing step.

FIG. 13 shows a cross-section of the annular member 10 of FIGS. 10-12 during the coextrusion step. During processing, a tubular structure is extruded containing a first coextruded material 165 and a second coextruded material 167. The first coextruded material 165 defines the annular member 10, discussed above. The second material 167 serves to position the folded structure of the annular member 10/first material 165. When the second material 167 is removed, the first material 165 is left behind in an unexpanded, folded state.

As shown in FIG. 13, during processing, the first coextruded material 165 defines the elongated annular member 10 having the circumferentially extending thick wall portion 162 where the thick wall portion 162 includes the first and second longitudinally extending ends 166, 168 as described above. During the coextrusion process, the second longitudinally extending end 168 overlaps and is exterior to the first longitudinally extending end 166 along a folded, overlapping segment 170. The thin wall portion 164 extends between the first and second longitudinally extending ends 166, 168 in a circumferential direction. The thin wall portion 164 is positioned radially farther from the central longitudinal axis of the coextruded tubular material than the first longitudinally extending end 166 and its adjacent thick wall portion 162. The thin wall portion 164 is positioned radially closer to the central longitudinal axis than the second longitudinally extending end 168 and its adjacent thick wall portion 162.

The second material 167 is coextruded between and in contact with the thick and thin wall portions 162, 164, in a manner that radially spaces the thin wall portion 164 from the thick wall portion 162. The second material 167 can be coextruded in two separate layers/portions to form the overlapping structure of the thick and think wall portions 162, 164. A first layer 172 of the second material 167 is positioned between the first longitudinally extending end 166 and the thin wall portion 164, and a second layer 174 of the second material 167 is positioned between the second longitudinally extending end 168 and the thin wall portion 164. Each of the first and second layers 172, 174 of the second material 167 have a generally C-shape in cross section. In some embodiments, the second material 167 extends circumferentially along the entire overlapping segment 170 and continues to extend away from the overlapping segment 170 in either direction, as shown in FIG. 13, and around at least a portion of the circumference of the thick wall portion 162. For example, the first layer 172 of the second material 167 extends circumferentially along the outer surface 176 of the annular member 10 and between the thin wall portion 164 and the thick wall portion 162 adjacent the first longitudinally extending end 166. The second layer 174 of the second material 167 extends circumferentially along the inner surface 178 of the annular member 10 and between the thin wall portion 164 and the thick wall portion 162 adjacent the second longitudinal end 168. This circumferential extension of the second material 167 provides support to the structure during the fabrication process. In the shown embodiment, the first and second layer 172, 174 each extend along the circumference of the annular member 10 by about 270-degrees. However, in other embodiments, the first and second layer 172, 174 may extend circumferentially only along the overlapping segment 170, about 45-degrees circumferentially, about 90-degrees circumferentially, about 135-degrees circumferentially, about 180-degrees circumferentially, about 225-degrees circumferentially, about 315-degrees circumferentially, or the first and second layers may extend a full 360-degrees circumferentially. The first layer 172 and the second layer 174 need not extend the same distance circumferentially. As illustrated in FIG. 13, the second material 167 has a wall thickness (measured in the radial direction) less than the thickness of the first material 165. The thickness of the second material 167 is uniform along the entire width of the corresponding first and second layer 172, 174, i.e., the circumferential width the first material extends along the circumference of the annular member 10. It is also contemplated, the that the thickness of the second material 167 may vary along the circumferential width of the first and second layers 172, 174. For example, the second material may have a tapering thickness such that the thickness of the second material is thicker in a circumferential central position of the first and second layer 172, 174, than at the edges of the first and second layers 172, 174.

After coextrusion, the second material 167 can be removed. In some implementations, the second material 167 can be physically removed from the first material 165 by force, for example, by applying a force (axial and/or radial) to at least one of the first and/or second materials 165, 167. The second material 167 can be formed of a material that does not adhere to the first material 165 during the coextrusion process, making its physical removal relatively easy. In other embodiments, the first material and second material can have different chemical properties or melting points, such that chemical or thermal treatments may be used to remove the second material 167 from the first material 165. While the first material 165 could be, or could incorporate, HDPE, the second material 167 could be, or could incorporate, nylon, polyethylene terephthalate, PA12, and/or polybutylene terephthalate, for example. The removal of the second material 167 enables the first longitudinal end 166 to slide relative to the second longitudinal end 168, such that the annular member 10 can be radially expanded.

In some embodiments, the coextrusion process used to form the sheath shown in FIG. 10 can include the formation of a taper tube 70, such as the one shown in FIG. 8 (i.e., a bump extrusion). Some methods include a step of covering the annular member 10 with the outer layer 50 after coextrusion. As discussed above, the outer layer 50 is formed of, or incorporates, a material with a lower elastic modulus than the annular member 10.

The use of the processing methods described above to form a folded sheath such as the one shown in FIG. 10 offers several advantages over conventional processes. The process takes less time and does not necessitate the use of costly heat shrink tubes (unlike annealing operations that could be used to form the folded profile). A vacuum is typically needed during extrusion of the folded annular member 10 to sustain a tubular shape during the extrusion process. This does not lend itself to formation of tube having a change in diameter. As a result, conventional sheaths are typically formed using several thermal bonding operations to create the transition from the distally located, folded, low profile cross section to the larger cross section at the proximal end (which is formed to mate with the hub/hemostasis valve housing). These operations add time and complexity to the process and incorporate failure locations at the bond joints. The coextrusion process described herein can be performed without running a vacuum because the second material 167 provides support to keep the tube round during coextrusion.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated. It is intended that the scope of the present invention herein disclosed should not be limited by the particular disclosed embodiments described above, but should be determined only by a fair reading of the claims that follow.

The invention claimed is:

1. A method of making an expandable sheath comprising:
coextruding a first material and a second material; and
removing the second coextruded material from the first coextruded material;
wherein the first coextruded material defines an elongated annular member having a circumferentially extending thick wall portion comprising a first longitudinally extending end and a second longitudinally extending end that overlaps the first longitudinally extending end, the thick wall portion being integrally connected to a circumferentially extending thin wall portion that extends between the first longitudinally extending end and the second longitudinally extending end of the thick wall portion; and
wherein the second coextruded material spaces the thin wall portion from the thick wall portion in a radial direction.

2. The method of claim 1, wherein the second coextruded material is removed by applying a force to at least one of the first and the second coextruded materials.

3. The method of claim 1, wherein the second coextruded material is removed from the first coextruded material by applying a thermal treatment to at least one of the first and the second coextruded materials.

4. The method of claim 1, wherein the second coextruded material is removed from the first coextruded material by applying a chemical treatment to at least one of the first and the second coextruded materials.

5. The method of claim 1, wherein removal of the second coextruded material allows for sliding movement of the first longitudinal end relative to the second longitudinal end and radial expansion of the elongated annular member.

6. The method of claim 1, wherein the second longitudinally extending end overlaps the first longitudinally extending end along an overlapping segment, and
wherein the second coextruded material extends along an entire circumferential width of the overlapping segment.

7. The method of claim 6, wherein the second coextruded material extends circumferentially away from the overlapping segment.

8. The method of claim 1, wherein the first longitudinally extending end is radially closer to a central axis of the elongated annular member than the thin wall portion, and the second longitudinally extending end is radially farther from the central axis the thin wall portion.

9. The method of claim 8, wherein a first layer of the second coextruded material is positioned between the first longitudinally extending end and the thin wall portion, and a second layer of the second coextruded material is positioned between the second longitudinally extending end and the thin wall portion.

10. The method of claim 9, wherein the first layer of the second coextruded material extends circumferentially from the first longitudinally extending end along an outer surface of the thin wall portion of the first coextruded material, and
wherein the second layer of the second coextruded material extends circumferentially from the second longitudinally extending end along an inner surface of the thin wall portion of the first coextruded material.

11. The method of claim 9, wherein the first layer of the second coextruded material extends circumferentially along an outer surface of the elongated annular member, and the second layer of the second coextruded material extends circumferentially along an inner surface of the elongated annular member.

12. The method of claim 1, wherein the second coextruded material extends along an inner surface and an outer surface of the elongated member.

13. The method of claim 1, wherein the second coextruded material extends around an entire circumference of an inner surface of the elongated member.

14. The method of claim 1, wherein the second coextruded material extends around an entire circumference of an outer surface of the elongated member.

15. The method of claim 1, further comprising adding a taper tube, the taper tube having a diameter greater than a diameter of the elongated member.

16. The method of claim 15, wherein the taper tube is added without using a thermal bonding process.

17. The method of claim 15, wherein the taper tube is added without using a bonding process.

18. The method of claim 15, wherein the taper tube is added as part of the coextrusion process.

19. The method of claim 1, further comprising covering the elongated annular member with an outer layer comprising a material having a lower elastic modulus than the elongated annular member.

* * * * *